US010266953B1

(12) United States Patent
Anthony

(10) Patent No.: US 10,266,953 B1
(45) Date of Patent: Apr. 23, 2019

(54) METHOD AND APPARATUS FOR THE MANUFACTURE OF COSMETIC SOLUTIONS USING ULTRAVIOLET LIGHT AND ELECTROLYSIS

(71) Applicant: Michael Mark Anthony, Hohenwald, TN (US)

(72) Inventor: Michael Mark Anthony, Hohenwald, TN (US)

(73) Assignee: KERATIN HOLDINGS LLC, Boca Raton, FL (US)

( * ) Notice: Subject to any disclaimer, the term of this patent is extended or adjusted under 35 U.S.C. 154(b) by 283 days.

(21) Appl. No.: 13/999,260

(22) Filed: Feb. 3, 2014

(51) Int. Cl.
| | |
|---|---|
| *A61K 8/34* | (2006.01) |
| *A61K 8/36* | (2006.01) |
| *A61K 8/41* | (2006.01) |
| *A61K 8/46* | (2006.01) |
| *A61K 8/49* | (2006.01) |
| *A61K 8/58* | (2006.01) |
| *A61K 8/73* | (2006.01) |

(Continued)

(52) U.S. Cl.
CPC ............... *C25B 3/02* (2013.01); *A61K 8/342* (2013.01); *A61K 8/345* (2013.01); *A61K 8/36* (2013.01); *A61K 8/416* (2013.01); *A61K 8/46* (2013.01); *A61K 8/49* (2013.01); *A61K 8/585* (2013.01); *A61K 8/737* (2013.01); *A61K 8/891* (2013.01); *A61Q 5/00* (2013.01); *B01J 19/123* (2013.01); *C25B 15/02* (2013.01); *A61K 2800/48* (2013.01); *A61K 2800/81* (2013.01); *A61K 2800/83* (2013.01)

(58) Field of Classification Search
CPC .......... A61K 8/46; A61K 8/891; A61K 8/737; A61K 8/342; A61K 8/416; A61K 8/345; A61K 8/49; A61K 8/585; A61K 8/36; A61K 2800/83; A61K 2800/81; A61K 2800/48; A61Q 5/00; C25B 3/02; C25B 15/02; B01J 19/123

See application file for complete search history.

(56) References Cited

U.S. PATENT DOCUMENTS 3,849,576 A * 11/1974 Kalopissis ............. A61K 8/447
424/70.51
4,482,435 A 11/1984 Torii et al.
(Continued)

FOREIGN PATENT DOCUMENTS

| FR | 2081566 | 12/1971 |
| FR | 2547728 | 12/1984 |
| GB | 1368232 | 9/1974 |

OTHER PUBLICATIONS

Amato, D.V., Thesis entitled "Latent Cysteine Residues from Polymers Prepared Via Free and Controlled Radical Polymerizations," presented to the Faculty of California Polytechnic State University, 89 pages, Jun. 2013.

(Continued)

*Primary Examiner* — Nicholas A Smith
*Assistant Examiner* — Colleen M Raphael
(74) *Attorney, Agent, or Firm* — Thompson Hine LLP

(57) ABSTRACT

The invention relates to the manufacture of cosmetic solutions for use on human hair using the effects of UV light and electrolysis. In particular, a specialized cross-linking of Hydrochloride protected thiols to form protected Thiazolidines is disclosed. The process uses both UV light and electrolysis to form stable cosmetic solutions that have a variety of uses.

37 Claims, 3 Drawing Sheets

(51) Int. Cl.
| | |
|---|---|
| *A61Q 5/00* | (2006.01) |
| *C25B 3/02* | (2006.01) |
| *A61K 8/891* | (2006.01) |
| *B01J 19/12* | (2006.01) |
| *C25B 15/02* | (2006.01) |

(56) References Cited

U.S. PATENT DOCUMENTS

| | | | | | |
|---|---|---|---|---|---|
| 4,801,445 | A | * | 1/1989 | Fukui | A61K 8/11 424/63 |
| 8,795,643 | B1 | * | 8/2014 | Anthony | A61Q 5/06 424/70.11 |
| 2003/0036490 | A1 | * | 2/2003 | Lorant | A61K 8/19 510/130 |
| 2006/0018867 | A1 | * | 1/2006 | Kawasaki | A61K 8/898 424/70.122 |
| 2008/0255498 | A1 | * | 10/2008 | Houle | A61C 17/02 604/20 |
| 2008/0264773 | A1 | * | 10/2008 | Searles | C02F 1/441 204/158.2 |
| 2008/0299059 | A1 | * | 12/2008 | Quadir | A61K 8/11 424/61 |
| 2009/0010855 | A1 | * | 1/2009 | Lepilleur | A61K 8/737 424/47 |
| 2013/0129639 | A1 | * | 5/2013 | Anderson | A61K 8/737 424/47 |

OTHER PUBLICATIONS

Neves-Petersen, Maria Teresa et al.; "UV Light Effects on Proteins: From Photochemistry to Nanomedicine"; Molecular Photochemistry—Various Aspects; InTech Open; pp. 125-158 (Mar. 30, 2012).

Amin, O.A.R. et al.; "Adsorptive and Catalytic Cathodic Stripping Voltammetric Determination of Timonacic"; Portugaliae Electrochimica Acta, 29(2); pp. 115-125; DOI: 10.4152/pea.201102115 (Mar. 31, 2011).

Osamu, Onomura et al.; "Memory of Chirality in the Electrochemical Oxidation of Thiazolidine-4-carboxylic Acid Derivatives"; Heterocycles, 80(2); pp. 1177-1185 (2010).

Bentley, Ronald; "Sarah Ratner 1903-1999, A Biographical Memoir"; National Academy of Sciences, Biographical Memoirs, vol. 82, pp. 221-241 (2003).

Smith, K.; "A Mixed Photoproduct of Thymine and Cysteine: 5-S-Cysteine, 6-Hydrothymine"; Department of Radiology, Stanford University School of Medicine; vol. 39, No. 6, pp. 1011-1016 (Mar. 23, 1970).

Gonzalez-Garcia, J. et al.; "Industrial Synthesis of Cysteine Derivatives"; European Research Conference: Organic Electrochemistry: Moving towards Clean and Selective Synthesis; 8 pages (Apr. 15-19, 1998).

Butvin, P.; "Complex Formation of Thiazolidine-2,4-dicarboxylic Acid with Selected Divalent and Trivalent Metal Ions"; Department of Pharmaceutical Analysis and Nuclear Pharmacy, Faculty of Pharmacy, Comenius University, SK-832 32 Bratislava; 4 pages (Jul. 18, 2001).

Incezdy, J.; "Analytical Applications of Complex Equilibria"; Ellis Horwood Ltd., England, p. 137 (1976).

Von Wandruszka, R. et al.; "Determination of sulfur species by cathodic square wave stripping voltammetry; Compounds relevant to natural sulfur mineralization"; Talanta, vol. 40, Issue 1; pp. 37-42 (Jan. 1993).

* cited by examiner

METHOD AND APPARATUS FOR THE MANUFACTURE OF COSMETIC SOLUTIONS USING ULTRAVIOLET LIGHT AND ELECTROLYSIS

BACKGROUND OF THE INVENTION

1. Field of the Invention

The present invention relates generally to the field of cosmetics. More specifically the present invention relates to a cost effective and novel method and apparatus for manufacturing a variety of creating cosmetic solutions using the similar concentrations of derivatives of Cysteine such as Cysteine hydrochloride and Keratin amino acids and aldehydes as starting materials. The preferred method includes the steps of subjecting a flow of cosmetic solutions to UV light at a flow speed of between 2 ft/sec to 200 ft/sec and an exposure radiation level of between 100 Joules/in3 of flow to 3000 Joules/in3 of solution by using an inline UV Radiation source such as a UV lamp. The method further includes electrolysis of said flowing solutions to controllably ionize the solution and to redeem Cysteine, hydrogen, sulfur and Chlorine gases and to generate unprotected Cysteine in situ for direct reactions to form a variety of Cysteine derivatives, including Thiazolidines and other thiol derivatives. This requires an exposure of a minimum of 0.1 to 500 Joules/in3 of energy density in the cosmetic solution in the form of UV radiation, electrolysis and thermal energy to get a minimal effect controlling effect on desired targeted end products. The combination of the amounts of UV radiation, the amount of electrolytic energy and the amount of heat energy, provide enough controlled energy to direct and target the reactions of Cysteine to desired percentages of end products.

BACKGROUND

As background to the present invention, it is noted that the manufacture of cosmetic solutions has generally involved the use of well-known chemicals that can be mixed to react and form solutions that have various applications to hair. Some are used to impart shine, smoothness and ease of styling. Other solutions are used to straighten, restructure and reshape hair. Since cosmetic solutions are used in general to influence the human hair structure, it is important that certain distinct properties of human hair be mentioned. The chemistry generally involves making cosmetic solutions by reacting chemicals in fixed molar proportions. However this method leads to competing reactions that sometimes have no controlling factors as to which reactants should preferably react and in what proportions they should react. There are no control measures when chemistry can be performed on a variety of reactants that compete for a given chemical species. Usually time ordered reactions permit preferred components to be created in order so that there is no competition for a chemical species that can react with several other chemicals in solution. The control of such reactions by purely physical parameters can result in a novel way to control preferred reacting species.

Description of Hair

Hair is made from keratin proteins that have a special structure forming long extended fibers with very good mechanical properties. The hair shaft comprises an outer protective layer of layered scales known as the cuticle layer. This cuticle layer has tiny elongated scales that overlap to form a covering around the hair shaft and this covering can open to allow access into the inner areas of the hair shaft. The cuticle layer is hydrophobic and does not get saturated with water and other chemicals and it is made from Cysteine proteins that form very hard strong matrices that have very good mechanical properties. Below this outer cuticle layer of scales is a layer of the cuticle structure that is very rich in Cysteine proteins called the exocuticle. This layer comprises about 37% of the total Cysteine protein-content of the cuticle layers. Just below the cuticle layer is a column of cells called the cortex. The cortex is made up a rigid network of strong cells and is mechanically the most important structure that controls the tensile, flexure, and shape of hair fibers. These cells are large and elongated and are aligned along the axis of the hair shaft forming the rigid network. This rigid network of cells is primarily made from Cysteine proteins and other amino acids held together by disulfide bonds. The disulfide bond is a covalent chemical bond binding two sulfur atoms together. As the hair grows, it builds these structural-meshes of covalently bound Cysteine proteins forming the general fiber shape of the hair. The shape of the fiber is determined by the manner in which the network of disulfide bonds is formed along the hair shaft. Kinks and bends occur as the general shape that the hair shaft takes for minimal stress from the forces of the disulfide bonds.

Cosmetic solutions are designed and manufactured to affect one or more specific layers of the hair structure to achieve a desired target effect. It is thus important that the manufacture of such solutions be designed and implemented to target the specific layers of the hair that require modification for the desired effects.

2. Description of the Prior Art

In the manufacture of cosmetics, UV light only has been used to kill bacteria, yeast, mold and fungus. Electrolysis is seldom used during manufacture of cosmetic products.

The Use of Ultraviolet Radiation During Manufacturing of Products

It is known that ultraviolet light, generally referred to as UV light, excites proteins and that proteins maintain the spatial proximity between aromatic residues of keratin amino acids (tryptophan, tyrosine and phenylalanine, Cysteine) with disulfide bridges (S—S), (Ref: *UV Light Effects on Proteins: From Photochemistry to Nanomedicine*; Maria Teresa Neves-Petersen, Gnana Prakash Gajula, and Steffen B. Petersen). The S—H bonds of Cysteine form nano-antennas that can capture UV light (from ~250-298 nm). It is also known that disulfide bridges (S—S) in Cystine are excellent quenchers of the excited state of aromatic residues, contributing to protein stability and activity. UV light excitation of the aromatic residues triggers electron ejection from side chains and these electrons can be captured by disulfide bridges leading to transient disulfide electron adduct radical which will dissociate leading to the formation of free thiol groups in the protein. This property can be used to effectively control manufacturing process of cosmetic solutions with targeted structures. Further, UV light affects the bond lengths of closed ring compounds such as Thiazolidines and as such, exciting these rings can lead to a preferential decomposition of the ring to release Cysteine to react with other compounds in solution.

There are three types of chemistries used in UV curing:

I) The first type of curing is Free Radical Curing, which is applied to acrylates and methacrylates. Free radicals of the R* form are generated by using a photo-initiator such as BenzoPhenone. BenzoPhenone-4 for example, is generally used in the manufacture of UV light inhibitors in cosmetic end products. However, it is only used to protect hair and skin from UV rays of sunlight and as such it is generally not used as a fixative agent during manufacture. It is simply added in cosmetic solutions to be used as a sun blocker when the final product is applied. Free radicals of photo-initiators generally attack an unsaturated bond, which may be opened so that affected molecules can be cross-linked by sunlight to form an effective sun-blocking layer on the skin or the hair.

II) A second type of UV curing uses thiol chemistry. UV light removes hydrogen removed from S—H functional groups to form a sulfur-charged species with an S—S bond. Proteins such as Cysteine form Cystine with a disulfide bond, RS—SR. These proteins are generally used in cosmetics to form protective films. The S—H functionalities in proteins are found on the hydrochloride protected amino acid L-Cysteine monohydrochloride and other types of amino acids. Because of Hydrochloride protection, the L-Cysteine monohydrochloride can also act as a self-photo-initiator requiring no external photoinitiators. When subjected to prolonged UV radiation, Cystine can undergo solutions the following types of effects can be observed:

$e_{aq}^{+}+RSSR \rightarrow /RSSR.^{-}$ $RSSR.^{-} \Leftrightarrow RS.+RS^{-}$

The free thiol can subsequently react with other free thiols in hair and keratin solutions to create new disulfide bridges. The effect of UV radiation on L-Cysteine Hydrochloride is also dramatic. (Ref: *A Mixed Photoproduct of Thymine and Cysteine: 5-S-Cysteine, 6-Hydrothymine*; Kendric C. Smith, Department of Radiology, Stanford University School of Medicine, Stanford, Calif.).

UV radiation causes the protected hydrochloride to become a free radical.

III) A third type of UV curing is cationic curing. UV light acts on a photoinitiator such as an Iodonium or Sulfonium metallic salt to generate a Bronsted acid. It the usual process, an epoxide ring is opened and linked to a polyol to form a UV-curable coating.

In cosmetic products UV protection is generally used to generate cross-linking during the use of the product to form sun blockers and it is rarely used to generate cross-linking during the manufacture of the cosmetic solution. The polymerization of Cysteine by thermosetting was discussed by San Luis Obispo in his Thesis, *Latent Cysteine residues from polymers prepared via free and controlled radical polymerizations*, (Faculty of California Polytechnic State University).

Polymerizing hydrogen by Thiazolidine linkages formed between Cysteine residues and poly(ethylene Glycol) macromers has been used as a sealant in cataract surgeries. Polymers containing free thiols have also been developed as muco-adhesives. Thiazolidine ring formation has also resulted in a wide variety of research in the conjugation of proteins by UV radiation to get new polymers in medical and cosmetic applications.

The Use of Electrolysis During Manufacture

Electrolysis is commonly used in the manufacture of products. For the purposes of the present invention, the use of electrolysis and UV radiation to control the concentration of Thiazolidine, Cystine, Cysteine, Keratin, and derivatives of Cysteine is disclosed. It is important to note that the electrolysis of L-Cystine Hydrochloride to generate L-Cysteine Hydrochloride is commonly known. However, the combination of the use of UV radiation to activate Cysteine S—H bonds to an reactive state for reactions in combination with its manufacture in situ is not disclosed in prior art.

The preferential excitation of the of UV light to decompose the Thiazolidine ring by means of the $^{+}NH2=CH$—R coupled with the excitation of the S—H bonds of Cysteine, coupled with the decomposition of the dimer Cystine to control the stock of Cysteine available for reaction with aldehydes and Phenoxyethanol is not disclosed in prior art. In general, the following tables show the competing factors for the formation of Cystine, Cysteine, Thiazolidines, and S-(2-Phenoxyethyl)Cysteine and their derivatives;

TABLE 1

| | Contribution of UV and Electrolysis to formation of compound | | | | | | |
|---|---|---|---|---|---|---|---|
| Compound | L-Cysteine Hydrochloride | L-Cystine Hydrochloride | Cysteine | Cystine | S-(2-Phenoxyethyl) Cysteine | 2-(2-Phenoxyethyl)-Thiazolidine-4-carboxylic acid | Thiazolidine |
| UV | − | + | − | − | + | − | − |
| Electrolysis | + | − | + | + | − | + | + |

Availability of aldehydes and reactive Cysteine S—H bonds assist the formation of the thiol-thiolate anion exchange:

$$R-S-H \Leftrightarrow R-S^{-}+H^{+} \quad (1)$$

This makes Cysteine reactive and ready to form Thiazolidines in the presence of aldehydes, but the completion from this excitation by UV also inhibits the formation of ringed Thiazolidines by excitation of the immonium ions with a structure:

$$^{+}NH2=CH-R. \quad (2)$$

The intensity of UV light required for reaction (1) is far less than that required for reaction (2) so the balance can be achieved by reducing exposure time of solutions to UV to either make reaction (1) prevail, or to make reaction (2) prevail.

a) Formation of Thiazolidines by means of fixation of Cysteine with aldehydes such as formaldehyde and Glyoxylic acid is well known. In a particularly interesting cosmetic product called Tri-ionic keratin that was created by the present inventor and referred to in cosmetic circles with the INCI name (International Nomenclature for Cosmetic Ingredients) Hydrolyzed Keratin (AND) Timonacic, Cysteine is reacted with formaldehyde to form Timonacic acid in the presence of keratin amino acids and p-benzoquinone.

b) U.S. Pat. No. 4,482,435 describes how to prepare a certain class of substituted Thiazolidine compounds with specific certain Thiazolidine as starting materials using electrolysis with lead oxide electrodes in Perchloric acid aqueous solution, halogenated organic solvents and a starting material of a substituted Thiazolidine. This does not require the breaking of the Thiazolidine rings. The invention shows that when 7-oxo-4-Thia-2,6-diazabiCyclo[3,2,0]hept-2-ene is electrolyzed in the presence of a two-phase mixture comprising a Perchloric acid aqueous solution and an organic solvent, selective reduction of the C=N double bond on the Thiazolidine ring takes place, giving a compound of the formula having the corresponding skeleton of 7-oxo-4-Thia-2,6-diazabiCyclo[3,2,0]heptane in a high yield. British Pat. No. 1,368,232 discloses a process for preparing the similar substituted Thiazolidine compounds form other Thiazolidines without breaking the ring.

c) In a paper published in Portugaliae Electrochimica Acta 2011, 29(2), 115-125 entitled *Adsorptive and Catalytic Cathodic Stripping Voltammetric Determination of Timonacic* (O. A. R. Amin, S. F. Belal, and R. Bakry), the electrolytic determination of Timonacic in tablet and solutions was examined.

d) J. Incezdy wrote a paper *Analytical application of complex equilibria*, Ellis Horwood Ltd., England, p. 137, 1976 on the anodic accumulation process takes place through the Thiazolidine ring opening due to the interaction of TC with mercury. A similar paper was written by R. Von Wandruszka, X. Yuan, M. J. Morra, in an article in *Talanta* 40 (1993) p 37-40.

e) In a paper entitled *Memory of Chirality in the Electrochemical Oxidation of Thiazolidine-4-carboxylic Acid Derivatives*, by Onomura, Osamu; Ng'aNg'a Wanyoike, George; Matsumura, Yoshihiro; Kuriyama, Masami, HETEROCYCLES, 80(2), pp. 1177-1185; 2010, the authors compare the electrochemical oxidation of Thiazolidines and corresponding oxazolidines in basic solutions as shown below.

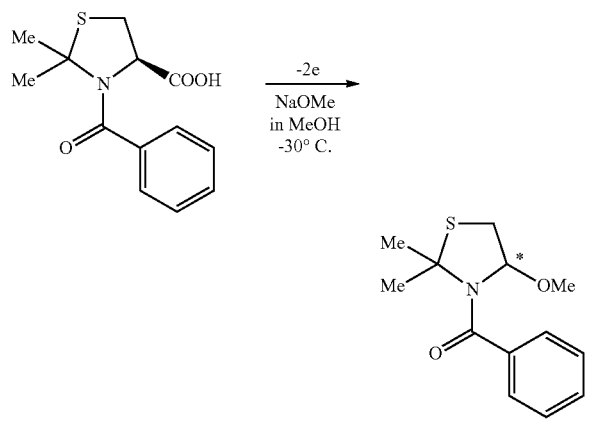

These investigations do not break the ring. They simply use the electro-potential of the charges of the ring to modify substitutions around the ring. However, prolonged exposure of the ring to UV radiation can break the ring to form new species.

f) French patent number 2547728, 24$^{th}$ of June, 1983, Riker Laboratories, shows how to make Thiazolidine carboxylic acid or Timonacic acid for medical uses.

The Use of Cysteine and Keratins in Cosmetics

The manufacture of cosmetic products using electrolytic processes is not commonly known. In a certain process developed by the present inventor to create a solution of ionized keratin called Tri-ionic Keratin (sold by Keratronics Inc. in Coral Springs, Fla.), a mixture of about 6% of Keratin by weight in aqueous solution is subjected to an electric current to induce a preferred ionization potential at the isoelectric point of Cysteine. Formaldehyde is added to react with the Cysteine content of the keratin to generate Thiazolidines-4-carboxylic acid in solutions in small yield. However, the purpose of the electric current is to simply generate a solution that has an electric potential that will make Cysteine amino acids in keratin particularly active for reactions with the aldehyde. Further, the amount of Thiazolidines formed is minimal since keratin only contains a small amount by weight of Cysteine, and only methionine amino acids contain sulfur molecules. The currents required are very high to essentially ionically fracture the keratin to generate charged Cysteine for reactions and further no UV light or electrolysis is used.

Problems Relating to the Use of Cysteine and Keratin in Cosmetic Solutions.

One drawback with the use of Cysteine in cosmetic solution formulations is that Cysteine readily oxidizes to the dimer Cystine. Therefore the removal of all oxygen is necessary and the water must be prepared with a careful procedure. Cystine is insoluble in water solutions and will generally not react with hair itself under normal conditions. Keratin is also highly insoluble in its natural form, and the use of keratin and Cysteine is only suitable for claims of skin formation and protection of hair solutions. One of the main problems that exist in prior art with the manufacture of cosmetic formulations that use Cysteine and keratin amino acids intended for use with human hair is that there exists no simple way to bind them as chemical structures that affect hair into compositions that can be easily manufactured without either degradation of critical components or reduction of their potential to act on hair in their various forms. For example, when Cysteine is placed in aqueous solution, it almost inevitably oxidizes to Cystine, and becomes inactive and unreactive to affect the sub-groups of amino acids of keratin in hair. Keratin has disulfide bonds and so is essential unreactive and insoluble in its normal form in aqueous solutions. It is this property of keratin that makes it so versatile as a bio-compound that makes stable parts such as hair, hoofs and nails. Cystine is also insoluble in aqueous solutions, and as such can only be used as a film former affecting the outer cuticles of the hair. The outer protective cuticle layer has tiny elongated scales that overlap to form a covering around the hair shaft and any film formation will inhibit the opening of the cuticle to allow access into the inner areas of the hair shaft. Thus when Cysteine and keratin are added to cosmetic solutions, Cysteine becomes Cystine and becomes ineffective within the cuticle and can only form films that do not affect the sub-cutaneous layer of hair.

Problems Relating to Thiazolidines as Ingredients in Cosmetic Solutions

Thiazolidines such as Timonacic acid are used in cosmetic products. The formation of Thiazolidines in cosmetic solutions can be inhibited if other compounds are present. Thiazolidines are generally formed by the reactions of an aldehyde with a sulfur compound that is reactive. Timonacic is formed by the reaction of formaldehyde and Cysteine. Formaldehyde is a very active compound and can react with many components such as Guar gums and other ingredients to form formaldehyde donors in cosmetic solutions. Further more, the decomposition of Thiazolidines-4-carboxylic acid (Timonacic) in hair solutions can result in the formation of Methylene Glycol, which has become a contested regulatory issue of formaldehyde donors in cosmetic solutions. Formation of Thiazolidines by means of fixation of Cysteine with formaldehyde is well known. In a particularly interesting cosmetic product called Tri-ionic keratin that was created by the present inventor and referred to in cosmetic circles with the INCI name (International Nomenclature for Cosmetic Ingredients) Hydrolyzed Keratin (AND) Timonacic, Cysteine is reacted with formaldehyde to form Timonacic acid in the presence of keratin amino acids and p-benzoquinone. No electrolysis is used and no UV light is used. Instead the keratin is ionized with an electric potential at the isoelectric potential of Cysteine, and then reacted with formaldehyde to generate Thiazolidines-4-carboxylic acid, which can then be used in cosmetic solutions for hair restructuring. However, in the concentrations needed for effective hair solutions, Thiazolidines-4-carboxylic acid is unstable and can easily decompose back to Cysteine and formaldehyde from the product.

Problems Relating to the Manufacture of Cosmetic Products Using Cysteine, and its Derivatives, Keratins, and Thiazolidines in Cosmetic Solutions Cysteine is reactive and can oxidize rapidly to Cystine. When Cysteine is placed in a cosmetic solution formulation, it rapidly becomes Cystine and then becomes unreactive. It is essentially a film former and does not survive after a few hours to act as an active ingredient that can affect the structure of the hair particularly when it forms Cystine as a film on hair. The cost of Cysteine and Cystine in pure form is also a factor. Cysteine costs about $200.00 per kg. Thus it is only used if the product costs can justify its end use. Further, its value in forming disulfide bonds with hair becomes inhibited by its polymerization to Cystine during manufacture. The cost of Thiazolidines is also a factor. Timonacic acid costs at the present time about $250.00 per kg. Thus it is only useful if it can be manufactured in situ during the manufacture of the cosmetic product. Cysteine hydrochloride is a much cheaper alternative as a source of Cysteine. However the invention is not limited to the use of L-Cysteine monohydrochloride or Cysteine hydrochloride. Cysteine in its pure form could also be in its pure form.

The main problem with the formation of Thiazolidines and Cysteine derivative in the manufacture of cosmetic solutions is that there is no way to effectively control the end products when aldehydes, Cysteine and other competing species of reactive chemicals are added to the solutions for reactions. Generally, one can bias the formation of Thiazolidines derivatives of Cysteine by using electric charges that make the solutions zwitterion at the isoelectric point of Cysteine. Cysteine and its derivatives oxidize to Cystine and since aldehydes do not attack Cystine, simply adding Cysteine in solution is not an effective way to form of Thiazolidines, and thus a major portion of the Cysteine is lost by oxidation to Cystine. No effective method exists for the continuous control of the concentration of available Cysteine and Keratins as active ingredients in cosmetic formulations to form in a controlled manner either Cysteine derivatives and keratin derivatives or Thiazolidines. No method exists for the continuous control of the preferential formation of Thiazolidines over other products during the manufacture of cosmetic solution that utilize them. Further the decomposition control of Thiazolidines cannot be achieved without a use of buffering solutions such as Sodium Hydroxide and acids that control pH of the solutions. To achieve direct control of the end products of formulation during manufacture, the present invention uses UV radiation and Electrolysis in conjunction with heat and controlled flow rates of solutions to attain a very good yield of targeted end products. Thus, simply regulating the physical parameters of flow, electric currents, and UV exposure energy and exposure time can target and control the balance between the end products of derivatives of Cysteine and Keratin.

It is thus an object of the present invention to provide a method of manufacture of cosmetic solutions that produces a variety of cosmetic solutions using chemical reactions catalyzed by UV radiation and by electrolysis.

It is another object of the present invention to provide such a method which permits the manufacturing targeted cosmetic formulations by controlling the reactions of targeted molecules of fixed amounts of reactants to form a variety of different cosmetic formulations.

It is still another object of the present invention to provide such a method which uses electrochemical decomposition of Cystine derivatives to provide a continuous supply of reactive Cysteine in situ to form desired derivatives of Cysteine.

It is yet another object of the present invention to use UV radiation to decompose ringed derivatives of Cysteine to open ring tautomer to control the concentration of said ringed derivatives.

It is a still further object of the present invention to use UV radiation to preferentially excite Cysteine S—H bonds for reactions with amino acids of keratin, aldehydes, acids and Phenoxyethanol to form an active form of keratin, Thiazolidines, and S-(2-Phenoxyethyl)Cysteine.

It is yet another object of the present invention to use UV sensitivity of the S—H functional groups of Cysteine to cross-link Cysteine and keratin amino acids to make targeted amounts of Lanthionine in a cosmetic solution.

It is an additional object of the present invention to use UV light to decompose the Thiazolidine ring by means of the $+NH_2=CH—R$ in other to limit their concentration in a cosmetic solution.

It is finally an object of the present invention to provide a method that is cost effective to manufacture a variety of cosmetic solutions.

SUMMARY OF THE INVENTION

The present invention accomplishes the above-stated objectives, as well as others, as may be determined by a fair reading and interpretation of the entire specification.

The invention relates to the manufacture of cosmetic solutions for use on human hair using the effects of UV light and electrolysis. In particular, a specialized cross-linking of Hydrochloride protected thiols to form protected Thiazolidines is disclosed. The process uses both UV light and electrolysis to form stable cosmetic solutions that have a variety of uses.

BRIEF DESCRIPTION OF THE DRAWINGS

Various other objects, advantages, and features of the invention will become apparent to those skilled in the art from the following discussion taken in conjunction with the following drawings, in which.

TABLE 2 shows the percent ingredients in various effects of the UV radiator and the electric cell.

DETAILED DESCRIPTION OF THE PREFERRED EMBODIMENTS

Figure 1:
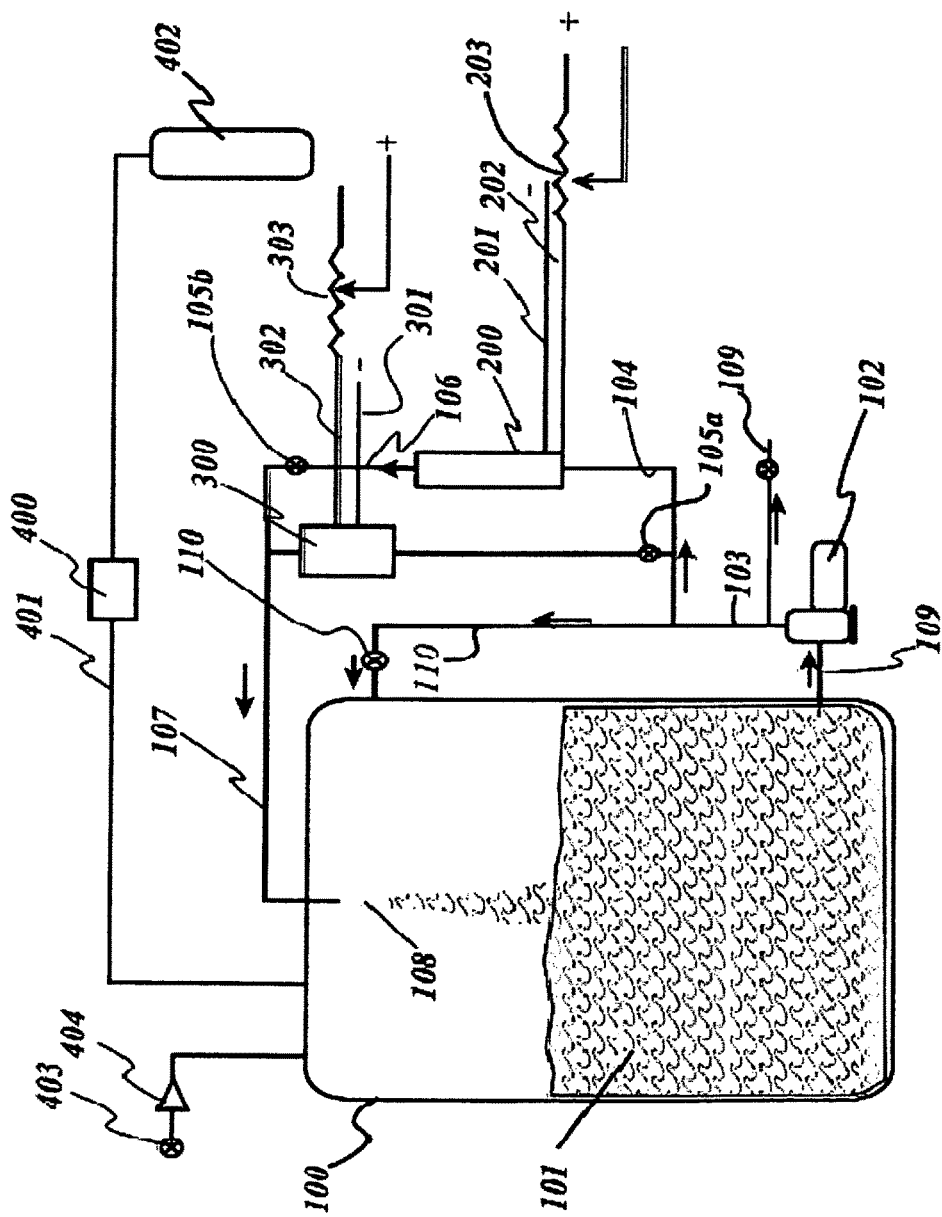
FIG. 1 is a drawing of the apparatus setup for manufacturing a variety of cosmetic solutions using UV light and electrolysis in a parallel configuration.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

The Present Invention

The present invention teaches a novel cost effective manufacturing method for a variety of cosmetic solutions using the same concentrations of derivatives of Cysteine such as Cysteine hydrochloride and Keratin amino acids and aldehydes as starting materials. A method and an apparatus are provided for practicing the method which uses UV radiation and electrolysis in conjunction with flow rates and exposure rates over time to create a variety of desired cosmetic products using Cysteine or a derivative of Cysteine such as L-Cysteine hydrochloride, Keratin amino acids, Phenoxyethanol and a suitable aldehyde or acid.

The present method uses a combination of the UV sensitivity of the S—H functional groups of Cysteine and the protection accorded by the hydrochloride to react Cysteine that is generated in situ with Phenoxyethanol, Glyoxylic acid, formaldehyde, and any aldehyde to create a controlled yield of S-(2-Phenoxyethyl)Cysteine and Thiazolidines respectively by inhibiting the dimer Cystine from being formed during electrolysis. L-Cysteine monohydrochloride is far cheaper than Cysteine and is more readily available. It is also very soluble in water. Further, the present invention teaches how to create a variety of cosmetic solutions using water, scented oils, L-Cysteine monohydrochloride, hydrolyzed keratin, Phenoxyethanol and a suitable acid or an aldehyde, thickening gums and waxes and silicone oils as a starting material.

Preferred Method

In practicing the invention, the following method may be used. The present manufacturing method includes the steps of subjecting a flow of cosmetic solutions to UV light at a flow speed of between 2 ft/sec to 200 ft/sec and an exposure radiation level of between 100 Joules/in$^3$ of flow to 3000 Joules/in$^3$ of solution by using an inline UV Radiation source such as a UV lamp. The method further includes electrolysis of said flowing solutions to controllably ionize the solution and to redeem Cysteine, hydrogen, sulfur and Chlorine gases and to generate unprotected Cysteine in situ for direct reactions to form a variety of Cysteine derivatives, including Thiazolidines and other thiol derivatives. This requires an exposure of a minimum of 100 Joules/in$^3$ of energy density in the cosmetic solution in the form of UV radiation, electrolysis and thermal energy to get a minimal effect controlling effect on desired targeted end products.

The combination of the amounts of UV radiation, the amount of electrolysis and the amount of heat, provide enough controlled energy to direct and target the reactions of Cysteine to desired percentages of end products. UV radiation targets quantum absorption of in the Cysteine molecules, while electrolysis targets the ionic bonds and electrolytic isoelectric potential energy. The heat is a simple thermal excitation source for the external momenta of the molecules in solution. Preferably the cosmetic solution consists of Keratin amino acids, Cysteine or Cysteine derivatives, such as L-Cysteine monohydrochloride, Dimethicone and other Silicone oils, Phenoxyethanol, a suitable alcohol wax, a natural gum such as Guar gum, and a suitable aldehyde or acid such as formaldehyde and or Glyoxylic acid. The wax could be Cetyl Stearyl alcohol or any non-charged suitable wax that can be used for viscosity regulation.

Waxes and oils that have been selected for this invention affect the electric potentials of the solutions and so affect the electronic association of targeted chemicals that are formed before said waxes are introduced into solution. Thus, the waxes and oils in particular, Cyclomethicone and Dimethicone, Butylene Glycol, Glycolic acid, Cetyl Stearyl alcohol, Behentrimonium chloride, Cetrimonium chloride, phenyltrimethicone, all act to stabilize the end products of reactions and also provide a host of suitable quaternary ammonium salt that is used in hair products with a large number of Carbon atoms and Hydrogen atoms with positively charge immonium group $NH_3^+$ termini. They can effectively bind and keep stable some of the charged-products obtained by the use of this invention. Propylene Glycol is a humectant and can bind oils and water as emulsions. The gums can also act to slow the decay of the charges of the solutions made as well as affect the viscosity of the end products.

The formation of Thiazolidines by condensation of Cysteine with formaldehyde is well known. In a particularly interesting cosmetic product called Tri-ionic keratin (INCI name: Hydrolyzed Keratin (AND) Timonacic), Cysteine is reacted with formaldehyde to form Timonacic acid in the presence of keratin amino acids and p-benzoquinone. No UV is used instead formaldehyde is used to generate Thiazolidines-4-carboxylic acid, which can then be used in cosmetic solutions for hair restructuring. However, this Thiazolidine is unstable and can easily revert back to donate formaldehyde from the product.

In the present invention, Cysteine in its protected form as L-Cysteine monohydrochloride and Keratin amino acids are made ionically reactive by the novel method of manufacturing a cosmetic solution using electrolysis and UV (ultraviolet) light.

It is known that the S—H bonds in Cysteine are light sensitive and act as photoinitiators. This property allows UV light to effectuate the reactive state of the S—H bond to allow the protected Cysteine to react with other chemicals while at the same time inhibiting the formation of the dimer Cystine. L-Cysteine monohydrochloride has the chemical structure:

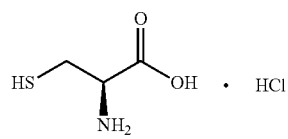

1,3-Thiazolidine-2,4-dicarboxylic acid is formed by the reaction of Cysteine and Glyoxylic acid. It has the structure:

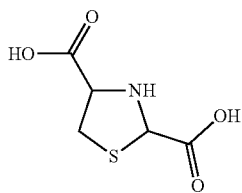 [SMILES: O=C(O)C1CSC(C(=O)O)N1]

Pure Cysteine can be used, however, the cost of pure Cysteine is far more than that of the protected hydrochlorides of Cysteine. The present invention allows the protected form to be also used since electrolysis can decompose the hydrochloride to the pure form of available Cysteine. To effectuate a reaction of L-Cysteine monohydrochloride and Glyoxylic acid or any aldehyde, the protection accorded by the hydrochloride must be taken into account, and UV light is well known to cause the S—H bond to facilitate thiol-thiolate anion exchange:

This makes it easier for Cysteine to react with other compounds. However, UV light also excites the immonium ions with a structure of $^+NH_2=CH—R$, where the mass and the stability of the ion depend on the side chain structure. Immonium ions sometimes undergo sequential fragmentation reactions yielding ion series characteristic for a particular amino acid. Thus, UV light can be used to open up the Thiazolidine ring and decompose it to its open ring structure to limit its formation in solution. Limiting the formation of Thiazolidines can then be used to control the amount of Cysteine available for reactions with other compounds such as Phenoxyethanol. The competition between electrolytic decomposition of Cystine.HCl to Cysteine.HCl and UV decomposition of Thiazolidines formed by such available Cysteine can result in controlled reactions of compounds that react with Cysteine. Advantageously, the stock of Cysteine can be directed toward reactions that limit the formation of Thiazolidines in a controlled manner.

Phenoxyethanol is a Glycol Ether often used as a preservative in dermatological products such as skin creams and sunscreen. It is a colorless oily liquid with the chemical formula $C_6H_5OCH_2CH_2OH$ and is a six-membered ring with an alcohol structure:

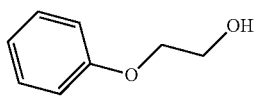

In the presence of intense UV light, one mole of Phenoxyethanol will rapidly react with one mole of Cysteine to form S-(2-Phenoxyethyl)Cysteine.

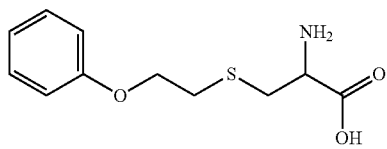 [SMILES: NC(CSCCOc1ccccc1)C(=O)O]

This can only happen if the Cysteine is created in situ otherwise Cysteine will oxidize at a very fast rate to the dimer Cystine with the structure:

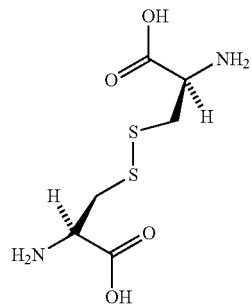

This polymerization will limit the availability of Cysteine for such a reaction. However, efficient use of UV radiation can enhance the formation of S-(2-Phenoxyethyl)Cysteine while electrolysis can limit the formation of Cystine. The competing reaction for the formation of Thiazolidines can be limited by UV radiation decomposition of the Thiazolidine ring to balance the available stock of Cysteine for reactions with Phenoxyethanol. The de-polymerization of Cystine can occur as follows:

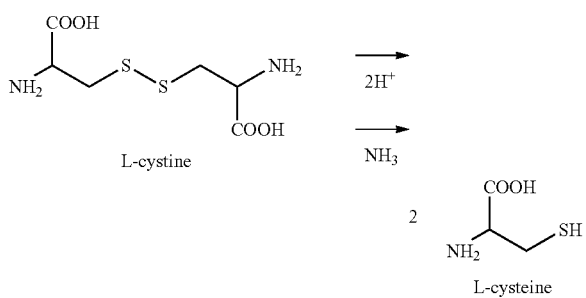

Cysteine is known to be highly reactive when formed in situ but difficult to pull from reacted molecules without using either highly acidic of highly basic conditions. The cathodic cleavage of disulphides produces two Cysteine residues and is known to be a very efficient method for obtaining pharmaceuticals such as, 1-Cysteine and homo-Cysteine and related products. Thus, any dimer formation by Cysteine can be overcome by continuous electrolysis to the monomer state again. (Ref: *European Research Conference: Organic Electrochemistry: Moving towards Clean and Selective Synthesis Industrial Synthesis of Cysteine Derivatives*, J. González-García, V. García-García, V. Montiel and A. Aldaz).

Advantageously, using electrolysis on a continuous stream of Cystine.HCl in solution can generate a constant attack on the dimer to make available for reactions in the monomer form, Cysteine, in situ.

The balance between the rapid excitation of the S—H bonds to make Cysteine quickly react, and the rapid electrolytic decomposition of Cystine dimer coupled with the rapid decomposition of the Thiazolidine ring in UV radiation, and the rapid reaction of Phenoxyethanol with Cysteine in UV light allow a process of manufacture of a range of cosmetic products to be developed using the same weight of starting materials. Advantageously, this makes the process of selection of particular grades of cosmetic products with certain preferred qualities easy to select by simply using a turn dial or switch electric rheostat for current modification to control the process with the intensity of current to a UV Radiator and an electrolytic cell and a flow rate control valve. This makes the chemistry of the process controllable by simple physical parameters.

Advantageously, when L-Cysteine monohydrochloride is dissolved in aqueous solution, it has a tendency to form the dimer by rapid oxidation and the dimer can then be electrolytically dissociated back to Cysteine using an electrolytic cell. The Cysteine thus formed has the advantage of being reactive and available to react in situ with Phenoxyethanol and aldehydes such as Glyoxylic acid to create a good yield of S-(2-Phenoxyethyl)Cysteine and Thiazolidine-2, 4-dicarboxylic respectively without the dimer Cystine being formed.

(Ref: *Complex Formation of Thiazolidine-2, 4-dicarboxylic Acid with Selected Divalent and Trivalent Metal Ions*, P. BUTVIN, M MITKOVÁ, J. SVĚTLÍK, and E. HAVRÁNEK, Department of Pharmaceutical Analysis and Nuclear Pharmacy, Faculty of Pharmacy, Comenius University, SK-832 32 Bratislava).

Sarah Ratner demonstrated how to prepare Thiazolidines-4-carboxylic acid by reacting formaldehyde with the protected form of Cysteine as L-Cysteine monohydrochloride, (Ref: National Academy of Sciences, *SARAH RATNER, 1903-1999; A Biographical Memoir* by RONALD BENTLE).

In her work, Sarah Ratner used Pyridine to deposit the Thiazolidines-4-carboxylic crystals from solutions of Thiazolidines-4-carboxylic hydrochloride. Of all the Thiazolidines, only the Thiazolidine-2,4-dicarboxylic (TIDA) is stable amongst all the Thiazolidines-carboxylic acids (TCA) derivatives, thus advantageously, decompositions that yield aldehydes can be avoided by restriction of the reactions of aldehydes with Cysteine to form the open ring Thiazolidine tautomer. This open ring tautomer can be delayed until all the Cysteine has been used up so that they can form stable Thiazolidine derivatives of other compounds such as 2-(2-Phenoxyethyl)Thiazolidine-4-carboxylic acid. However, if properly combined, the equilibrium of Thiazolidine-4-carboxylic acid and its protected hydrochloride form can be used to offset any decomposition equilibrium to the left. The use of Thiazolidine-2, 4-dicarboxylic is proposed in a French Patent number 2081566 for pharmaceutical formulations. However, the use of L-Cysteine monohydrochloride to create highly reactive and excited thiolate of Cysteine in situ by electrolysis and then reacting it with Glyoxylic acid to form the Thiazolidine-2, 4-dicarboxylic is not mentioned in literature.

The functions of the remaining ingredients that are specified according to the listed percentages for the purposes of the invention are as follows:

Cyclomethicone and Dimethicone act as shine and lubricants in the hair. They also serve to help deter any further electrolytic charge reactions due to an excess of oxygen that may remain in the solutions during electrolysis and after manufacture.

Guar Gum acts as a viscosity modifier in solution. It should be preferably non-cationic. Unlike usual cationic Guar Gums used in cosmetics, it is preferable that the selection of this gum be made from food-grade gums rather than from cosmetic grade gums. Cationic gums are sensitive to charges.

Cetyl Stearyl alcohol acts as a thickener in conjunction with the gums. Behentrimonium chloride is a suitable is a quaternary ammonium salt that is used in hair products with a 25 Carbon atoms and 55 Hydrogen atoms with a positively charge immonium group $NH_3^+$ terminus. It can effectively bind to charged-products used in this invention if needed.

Cetrimonium chloride is a suitable is a quaternary ammonium salt that is used in hair products with a 19 Carbon atoms and 42 Hydrogen atoms with a positively charge immonium group $NH_3^+$ terminus. It can effectively bind to charged-products used in this invention if needed.

Butylene Glycol and Glycolic acid are a humectant and can bind oils and water as emulsions. Propylene Glycol is a humectant and can bind oils and water as emulsions. Xanthan Gum is a cationic thickener that helps bind the solution together if a particular viscosity is desired at low pH values. Caprylyl Methicone is an emollient that helps with the shine imparted by the solution on hair.

To manufacture a variety of differing solutions, a mixture of water, Hydrolyzed Keratin powder, a Cysteine source such as L-Cysteine monohydrochloride, an aldehyde such as one of Glyoxylic acid and Formaldehyde, and Phenoxyethanol are used together with UV radiation and electrolysis to achieve targeted cosmetic formulations with various advantages. Other ingredients such as Cyclomethicone and Dimethicone, Guar Gum, Cetyl Stearyl alcohol, Behentrimonium chloride, Cetrimonium chloride, Butylene Glycol, Glycolic acid, Propylene Glycol, Phenyltrimethicone, are added in the solution to stabilize and emulsify the solution for use in a variety of cosmetic products. Glyoxylic acid and formaldehyde are examples of aldehydes that can be used in the invention to form Thiazolidines and their derivatives.

It is important to note that a fixed percentage composition of ingredients can create a variety of cosmetic compositions by so to speak "dialing the electric and turning the valve". Thus if a certain mix of the chemicals is already in the tank, the formulator can then decide to dial in which end products he or she desires by electrolysis and UV radiation. The aldehyde such as one of Formaldehyde and Glyoxylic acid, and the Phenoxyethanol, are respectively the molar equivalent of half the Cysteine content since they compete for reactions with Cysteine. Formaldehyde may be used in conjunction with Glyoxylic acid if Thiazolidine-4-carboxylic acid and Thiazolidine-2, 4-dicarboxylic are both targeted to be formed in solution.

The initial starting solution, also referred to as a first cosmetic solution, consists of water heated to about 150° F. in a plastic tank. A fixed amount of Hydrolyzed Keratin powder, a source of Cysteine, such as L-Cysteine monohydrochloride, Phenoxyethanol and an aldehyde such as one of Glyoxylic acid and or formaldehyde, or a mixture of both are added into the heated tank of water and circulated by a pump for about 1 hour until they have thoroughly mixed. The heated starting solution is then circulated by a fluid pump through an Electrolytic cell and a UV Radiator. The choice of the aldehyde depends on the types of ringed Thiazolidine that is targeted in the final solution. Formaldehyde will yield Thiazolidine-4-carboxylic acid, while Glyoxylic acid will yield Thiazolidine-2, 4-dicarboxylic.

Preferably, simple pumps and mixers are used to circulate the fluids and the flow circuit is designed so that a valve can adjust the amount of flow rate through the electrolytic cell and the UV Radiator. Preferably plastic tanks are used to eliminate the loss of electrostatic potentials, however, one must be careful to selects tank materials that can withstand the temperature of the process. High Density Polyethylene (HDPE) or Polypropylene will suffice for the tank material, and PVC piping will also suffice. HDPE can withstand temperatures below 180° F. since its melt point is about 248° F. to 356° F. Steel tanks can be used if properly prepared for electrical safety.

The mixture is circulated through an off-the-shelf de-chlorination Electrolytic cell, which in this case was modified from a de-chlorinator system made by AquaCal Auto-Pilot, Inc., 2737 24th Street North, St. Petersburg, Fla. 33713. The Electrolytic cell uses a standard 230 VAC supply at 30 amps. Considering the pKa values, Cysteine is in the Zwitterion form (HSCH2CHNH3$^+$COO$^-$) in solution at Cathodic peak of 0.64 V a low voltage can be used to dissociate the dimer Cystine to Cysteine. However the Electro-potential needed to dissociate the Cl$^-$ ion can be varied from 1V DC to 12V DC. The current ultimately determines the amount of Hydrogen, H$^+$, and Chlorine, CL- that can be released from solution over a given time. As an example, a combination of four inline AutoPilot electrolytic systems can easily process about 8 Kgs of hydrochloride protected Cysteine material for a sample batch of 1000 kg of cosmetic solution in 10 to 15 hours of operation. The electrolysis requires a minimum of 0.10 Joules/in$^3$ of energy per cubic inch of cosmetic solution at the maximum percentage range of 0.8% L-Cysteine hydrochloride in such a solution to have a desired effect, since the amount of electrons needed to completely dissociate the amount of L-Cysteine hydrochloride in this amount of solution requires this amount of electrical energy to be consumed.

The flow is passed through a UV light Radiator which in this case can be built from one or a series of SMART HO UV Sterilizers made by Emperor Aquatics Inc., located at 2229 Saratoga Station Road, Pottstown, Pa. 19464. An exposure of a minimum of 100 Joules/in$^3$ of cosmetic solution at the minimum percentage range of 0.3% Cysteine in such a solution is required to get a minimal effect of the UV light.

To manufacture a particular cosmetic solution, the amount of exposure time to both the UV radiation and Electrolytic cell are estimated respectively. The following examples give estimates for different types of solutions obtained by the process.

A) Solutions with Maximized Yield of S-(2-Phenoxyethyl)Cysteine.

As an example of manufacturing 1000 kg of the cosmetic solution A with a maximized yield of S-(2-Phenoxyethyl) Cysteine, purified water is first added to a tank and heated to about 150° F.

First, Hydrolyzed Keratin, and a source of Cysteine such as L-Cysteine monohydrochloride are added to the water. Cysteine and Cysteine-sources are used interchangeable sine they all provide a source of the reactant Cysteine. Advantageously, L-Cysteine monohydrochloride, and L-Cysteine hydrochloride can equally used as a source of pure Cysteine in all the invention. In this case as an example, about 5 kg of Hydrolyzed Keratin powder, and about 80 kg of L-Cysteine monohydrochloride are added to about 800 kg of water in a tank and then thoroughly mixed by circulating the solution through with a pump. The solution is heated to 150° F. while circulating by a pumping means, then, an aldehyde such as Glyoxylic acid (100 kg) or formaldehyde (90 kg) is added and rhen, 20 kg of Phenoxyethanol is added to the mixture.

Liquid hydrolyzed keratin can also be used, in which case about 50 kg of the liquefied form is added. After circulating this mixture through the tank for about an hour, both the UV Radiator and the Electrolytic cell are turned on. The mixture is circulated for at least five hours through both the UV Radiator and the Electrolytic cell to allow hydrogen and Chlorine to be removed from the L-Cysteine monohydrochloride by electrolysis and to decompose the Cystine hydrochloride back to the monomer as a available Cysteine for reactions. During this period, in situ Cysteine is generated as an unprotected Thiol and it immediately reacts with competing molecules of Phenoxyethanol and if Glyoxylic acid is used, it will S-(2-Phenoxyethyl)Cysteine and Thiazolidine-2, 4-dicarboxylic respectively.

However, the Thiazolidine-equilibrium is affected by UV radiation and it is decomposed at a rate determined by the intensity of the UV light in Joules/in$^3$. The decomposed Thiazolidine makes Cysteine available to react with Phenoxyethanol. By balancing the amount of unprotected Cysteine generated and the equilibrium point of the Thiazolidine formation and decomposition, the yield of S-(2-Phenoxyethyl) Cysteine can be maximized during the process as it preferentially reacts with Cysteine under UV light. A continuous flow speed of between 30 in/s to 40 in/sec through the process pipe and the UV Radiator to ensure an exposure radiation level of between 100-3000 Joules/in$^3$ is achieved from one or more of UV radiator lamps. This intensity of UV light can vary depending on the density of the fluid and the opacity. However these factors can be nulled out if the process repeats and exposes every molecule to the radiation field. Varying the flow rate will vary the delivery of total rate of energy exposure of UV light in Joules/in$^3$ of solution and this in turn regulates the rate of decomposition of Thiazolidines compounds formed by reactions between Cysteine formed in situ by electrolysis and Glyoxylic acid. The electrolysis regulates the rate of formation of the dimer Cystine to make Cysteine valuable at prescribed quantities for reactions. Cysteine is continuously formed by electrolysis and consumed as required. However in some cases, one could adjust the Electrolytic cell to also regulate the rate of yield of Cysteine.

The removal of Chlorine from the anode of the Electrolytic cell at voltages greater than 5V can be effectuated by flowing excess gases from the main processing tank through a condenser pipe into a smaller separate chlorinator tank. Preferably a MAGDOS LT dosing pump with a Solenoid-driven diaphragm made by Lutz-Jesco GmbH located in Wedemark, Germany, is used to remove excess Chlorine from the process tank and transfer it to the chlorinator tank. Dosing pumps are used in many branches of industry that work with liquid chemicals including toxic and aggressive media. The Chlorine generated from the Electrolytic cell is sucked from the tank and replaced by air to displace the unwanted gas while no Chlorine escapes into the atmosphere. The Chlorine gas is passed through a series of water filled plastic containers to absorb the Chlorine and make HCl solution, which can be used in the factory for cleaning purposes. Throughout the process run time of the Electrolytic cell, Chlorine gas is continuously removed from the process and separated from the cosmetic solution.

Thus, the freed Cysteine in situ can readily react with Phenoxyethanol to maximize the yield S-(2-Phenoxyethyl) Cysteine. The rate of formation of S-(2-Phenoxyethyl)Cysteine depends only on the free Cysteine available in situ and the intensity of the UV light. Once all the Phenoxyethanol is consumed, the amount of Thiazolidines will remain constantly held to a fixed equilibrium value by UV decomposition, leaving Cysteine in solution to form the dimer Cystine or bond with other amino acids of keratin and not to further react. This process will give nearly 70-80% yield of S-(2-Phenoxyethyl)Cysteine and about a 10%-15% yield of Thiazolidines after 10 hours of operation. Since the protected hydrochloride of Cystine can also reform in solution, the extent of further electrolysis determines the amount of unprotected yield of available Cysteine to form chloride-free Thiazolidines. If the solution is left to continue running through the electrolytic cell for at least 10 hours Cystine-hydrochloride will be formed at the expense of the inhibited Thiazolidines. So the amount of Thiazolidines formation can be accurately regulated. If left to run through the Electrolytic cell and UV light for up to 15 hours, the hydrochloride is removed and the pure dimer can be decomposed in this process back to Cysteine. Further UV light also fractures keratin amino acids to smaller fragments by the process:

Fracturing of Keratin disulfide bonds using UV

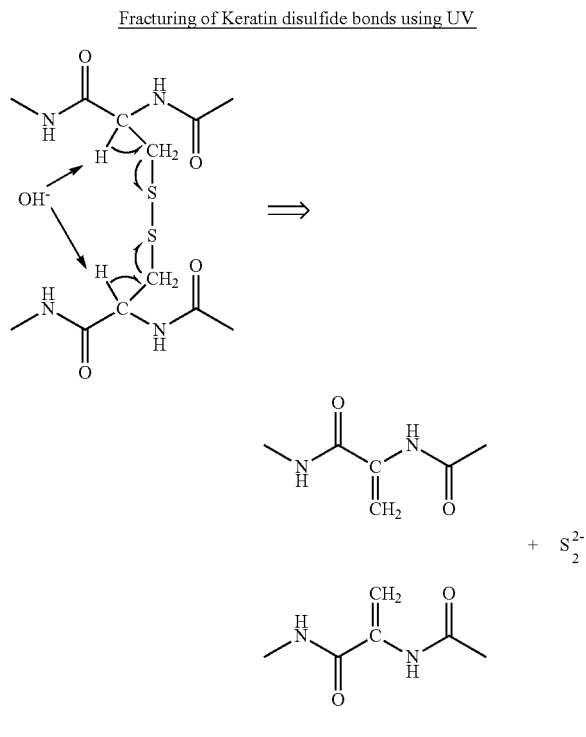

During the process, negatively charged sulfur ions can either be removed at the cathode as hydrogen sulfide gas or left in solution to form Lanthionine:

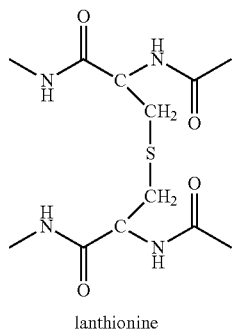 [SMILES: CNC(=O)C(CSCC(NC(C)=O)C(=O)NC)NC(C)=O]
lanthionine

Cysteine can also form sulfur cross-bridges with the keratin leaving the amount of Thiazolidine-2, 4-dicarboxylic regulated as desired.

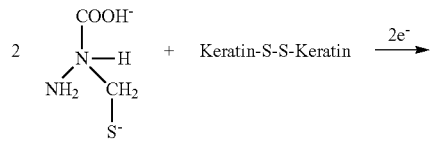

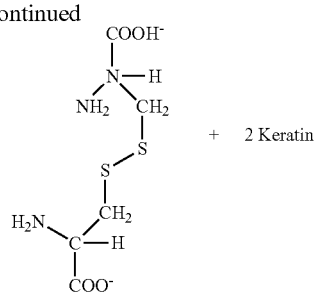

If formaldehyde is used in place of Glyoxylic acid, Thiazolidine-4-carboxylic acid will be formed, and the rate of such formation can also be regulated as desired. Advantageously, the UV exposure process and the electrolysis can each be regulated independently to provide any yield of Lanthionine needed for the solution. Lanthionine can penetrate the cuticle and restructure hair by recreating disulfide bonds when the cosmetic solution is used on hair. Alternatively, the modified keratin proteins can react with hair containing methyl groups to form disulfide bonds on the hair. Further, there is synergetic action between the Phenoxyethanol, Cysteine, and the electrolysis and UV process, which generates hydrogen and oxygen and with the presences of sulfur ions in solution some sulfated compounds will be generated.

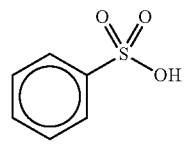

The presence of Thiazolidines, Cysteine-derivatives, and Keratin-derivatives with an excess of methylene groups accords advantages to cosmetic solutions. Methylene bridges could be formed with hair keratin, and depending on the level of each such ingredient, the cosmetic product can be tailored to produce differing effects on hair using the same chemicals. The solution thus created is generally light amber in color, but the color can vary depending the amounts of Thiazolidines generated by the process. Thus colorimetrics could also be used to regulate the process.

The remaining ingredients including Silicone oils, gums, and Cetyl Stearyl alcohols can be added to emulsify and thicken the solution. In general to complete solution of the example given of making 1000 kg of the cosmetic solution, about 40 kg by weight of Cyclomethicone and Dimethicone (the 50%/50% mix), 20 kg by weight of Guar Gum, 2 kg by weight of Behentrimonium chloride, 2 kg by weight of Cetrimonium chloride, 10 kg by weight of Butylene Glycol, 10 kg of Glycolic acid, 10 kg by weight of Propylene Glycol is further added into the circulating heated water and the resulting mixture is circulated for an additional period of time but not less than one hour, until all the waxes have melted completely and a homogenous mixture is obtained. The additional amount of water added is calculated to bring up the total weight of the solution to 1000 kg after all the ingredients are accounted for. Thus it is preferable to start with about 800 kg of water if a batch of 1000 kg of solution is to be made. The gums and waxes can adjusted in the solution A to give the desired viscosity of between 1000 cps to 5000 cps at room temperature (78° F.). The solution is then left to cool to room temperature with the electrolytic cell turned off and the UV lamps turned off.

B) Solutions Rich in Thiazolidines.

As an example of manufacturing 1000 kg of the cosmetic solution B with a maximized yield of Thiazolidines using the same ingredients, the starting solution is made by adding purified water to a tank and heated to about 150° F. The this starting water is also heated by the UV radiator 200 and so the heaters must be cautiously turned off during the process after the solution reaches 150° F. If the setup intends to use the UV Radiator at maximum intensity of 3000 Joules/in$^3$, then no extra thermal heating is required since the UV light itself will heat the solution to about 150° F. To heat 1000 kg of water 150° F. from room temperature (78° F.), requires 40,000 kCals or 167,360 KJ. This is an energy density of 2,740 Joules/in$^3$. Thus, the UV light can effectively heat the solution to 150° F. as needed. 150° F. is just an example of a suitable temperature for the process, but the solution can be made at temperatures below the boiling point.

First, Hydrolyzed Keratin and a Cysteine sourcing compound such as L-Cysteine monohydrochloride are added to the water according to the percentages listed in Table 2. In this case as in the prior example, about 5 kg by weight of Hydrolyzed Keratin powder, 80 kg by weight of L-Cysteine or a source of Cysteine such as L-Cysteine monohydrochloride, are added to about 800 kg of water in a tank and then thoroughly mixed by circulating the solution in the tank with a pump. Hydrolyzed Keratin in liquid form can also be used, in which case about 50 kg of the liquefied form is added. The solution can be preheated using electric or propane heaters to about 150° F. Continuing this example of making 1000 kg of the solution, 60 kg of Glyoxylic acid and 20 kg by weight of Phenoxyethanol are added to the mixture. A continuous flow speed of between 100 in/s to 130-160 in/sec is maintained through the process pipes to ensure that prolonged UV radiation exposure levels can be achieved from the UV Radiator. The intensity of UV radiation depends on the density of the circulating fluid and its opacity. However these factors can be nulled out if the process repeats and exposes every molecule of the solution to the radiation field until a certain total UV energy has been delivered. Varying the flow rate will vary the energy density delivery and this in turn regulates the rate of formation and decomposition of Thiazolidines compounds formed by reactions between Cysteine that is formed in situ by electrolysis and the aldehyde, which in this case is Glyoxylic acid. If a protected form of Cysteine such as the hydrochloride is used, the electrolysis current can be regulated to allow Thiazolidine-hydrochlorides to first form from the mix so that they can be electrolyzed to yield the unprotected Thiazolidines. Since Cysteine has been observed to react faster with aldehydes such as Glyoxylic acid than with Phenoxyethanol in UV light, the rate of Thiazolidine-formation is maximized at the expense of S-(2-Phenoxyethyl)Cysteine. The mixture is circulated with both an active UV Radiator and an active electrolytic cell. The mixture is circulated for at least five hours through both the UV Radiator and the electrolytic cell to allow hydrogen and Chlorine to be removed from the L-Cysteine monohydrochloride by electrolysis. To ensure total exposure of every molecule of the solution to UV light and electrolytic, a period of time is required for the process. However, it is the energy density that determines the process, so the total energy delivered per cubic inch of solution determines the quantum reactions that occur to decompose the compounds using the UV radiation or electrolysis. After 5 hours, the UV light can be turned off to allow Thiazolidine formation. This allows the Thiazolidines to form without UV decomposition to deter their rate of formation. This process will give nearly 50-60% of the maximum possible Thiazolidine-yield after 10 hours of operation and about 70%-80% S-(2-Phenoxyethyl)Cysteine yield. Adjusting the time the UV Radiator is left active can regulate the amount of Thiazolidines formed. For example if the Thiazolidine contents needs to be tuned down, the UV lights could be turned on again for a period of time. In general about 10% of the total possible yield (no more than 80%) is obtained per hour of operation without the UV Radiator being turned on. Since the hydrochloride of Cysteine can also reform in solution, the extent of further electrolysis determines the amount of unprotected Cysteine-yield that will be available to form chlorides of Thiazolidines. The removal of Chlorine gas from the anode of the Electrolytic cell at voltages greater than 5V can be effectuated by flowing the excess gases from the tank through a condensation pipe into a smaller separate chlorinator tank that is filled with water or a suitable basic solution. Preferably a MAGDOS LT dosing pump with a Solenoid-driven diaphragm made by Lutz-Jesco GmbH located in Wedemark, Germany, is used to remove excess Chlorine from the process tank and transfer it to the chlorinator tank. Dosing pumps are used in many branches of industry that work with liquid chemicals including toxic and aggressive media. The Chlorine generated from the Electrolytic cell is sucked from the tank and replaced by air to displace the unwanted gas while no Chlorine escapes into the atmosphere. The Chlorine gas is passed through a series of water filled plastic containers to absorb the Chlorine and make HCl solution, which can be used in the factory for cleaning purposes. Throughout the process run time of the Electrolytic cell, Chlorine gas is continuously removed from the process and separated from the cosmetic solution.

If the solution can be left to continue running through the electrolytic cell for at least 15 hours if the dimer Cystine-hydrochloride is to be completely eliminated so that all the available Cysteine will be used up. Simply deciding when to turn the electrolytic cell off can regulate the dimer concentration over time. Thus, the amount of Thiazolidine-formation and the dimer, Cystine, can also be accurately regulated. The UV light also fractures keratin amino acids to smaller fragments by the process:

Fracturing of Keratin disulfide bonds using UV

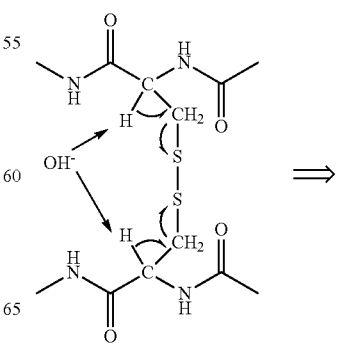

-continued

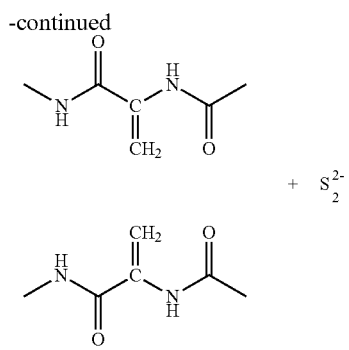

If the UV light is left on for a period exceeding 10 hours, this fracturing will start to occur and Lanthionine will be formed as a by-product. During the process, negatively charged sulfur ions can either be removed at the cathode as hydrogen sulfide gas or left in solution to form Lanthionine:

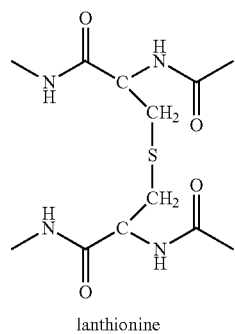 [SMILES: CNC(=O)C(CSCC(NC(C)=O)C(=O)NC)NC(C)=O]

lanthionine

Cysteine can also form sulfur cross bridges with the keratin amino acids. If there is an excess of Cysteine after all the dimer has been used up by electrolytic dissociation, the excess Cysteine can react with keratin amino acids through the methylene bridges. Advantageously, the UV exposure length can be regulated to provide any yield of Lanthionine needed for the solution. Lanthionine can penetrate the cuticle and restructure hair by recreating disulfide bonds when the cosmetic solution is used on hair. Alternatively, the modified keratin proteins can react with hair containing methyl groups to form disulfide bonds on the hair. Further, there is synergetic action between the Phenoxyethanol, Cysteine, and the electrolysis process generates some hydrogen and oxygen and with the presences of sulfur ions in solution some sulfonated compounds will be generated.

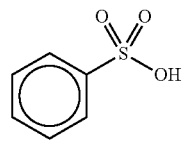

The presence of Thiazolidines, Cysteine-derivatives and keratin-derivatives with an excess of methylene groups accords advantages to cosmetic solutions depending on their concentrations. Methylene bridges could be formed with hair keratin, and depending on the level of each such ingredient, the cosmetic product can be tailored to produce differing effects on hair using the same chemicals. The solution thus created is generally amber in color, but the color can vary depending the amounts of Thiazolidines generated by the process.

To stabilize the solution, and make it suitable for cosmetic use, the remaining ingredients including scented oils, silicone oils, gums, and Cetyl Stearyl Alcohol can be added to finalize the solution. In general to complete solution B, 40 kg of Cyclomethicone and Dimethicone, 20 kg of Guar Gum, 2 kg of Behentrimonium chloride, 2 kg of Cetrimonium chloride, 10 kg of Butylene Glycol, 10 kg of Glycolic acid, 10 kg of Propylene Glycol is further added into the circulating heated water and the resulting mixture is circulated for an additional period of time but not less than one hour, until all the waxes have melted completely and a homogenous mixture is obtained. The additional amount of water added is calculated to bring up the total weight of solution to 1000 kg after all the ingredients are accounted for. Thus it is preferable to start with about 800 kg of water if a batch of 1000 kg of solution is to be made. The gums and waxes can adjusted in the solution to give the desired viscosity of between 1000 cps to 5000 cps at room temperature (78° F.). The solution is then left to cool to room temperature with the electrolytic cell turned off and the UV lamps turned off.

Advantageously, as a demonstration of the advantage of this method of manufacture of cosmetic solutions containing Glycols and aldehydes, if methylene Glycol (formaldehyde+water) is used to react with Cysteine hydrochloride to form the protected Thiazolidines-4-carboxylic acid hydrochloride, the hydrochloride can be left in its protected form so that it does not easily decompose to donate the Glycol thus preventing the release of formaldehyde or the aldehyde in general. By regulating the formation of Thiazolide-4-carboxylic acid and the hydrochloride, Thiazolidine-4-carboxylic acid hydrochloride, the equilibrium of the Cysteine-formaldehyde can be shifted advantageously toward the protected Thiazolidine-hydrochlorides and away from the Glycol. Further, it is known that in the presence of formaldehyde, S-(2-Phenoxyethyl)Cysteine will form 2-(2-Phenoxyethyl)Thiazolidine-4-carboxylic acid which is more stable in aqueous solutions than its decomposition product Thiazolide-4-carboxylic acid. Table 2 below shows the various percentages of ingredients obtained in percentage ranges after experiments performed on the specified ingredients. Other ingredient effects on Cysteine concentrations are listed as "Other".

Advantageously, the invention allows one to preferentially limit the formation of a thermodynamically favorable reaction product such as Cystine and S-(2-Phenoxyethyl)Cysteine in place of Thiazolidine derivatives which take some time to form from Cysteine. Thus, if without the effects of UV radiation and electrolysis one were to just add the same percentages as shown in Table 2 of the reactants Hydrolyzed Keratin, L-Cysteine monohydrochloride, Glyoxylic acid, formaldehyde and Phenoxyethanol to water, the thermodynamic equilibrium will cause all the protected Cysteine to oxidize to L-Cystine-hydrochloride without forming any other component in significant quantities. To achieve a controlled distribution of Cysteine molecules among the reactants, one must use UV light and electrolysis to control the formation of Thiazolidines, Cystine and S-(2-Phenoxyethyl)Cysteine, so that each such product of reaction will manifest in certain controlled percentages by biasing the reaction in favor of the products needed.

TABLE 1 (repeated)

Contribution of UV and Electrolysis to formation of compound

| Compound | L-Cysteine Hydrochloride | L-Cystine Hydrochoride | Cysteine | Cystine | S-(2-Phenoxyethyl) Cysteine | 2-(2-Phenoxyethyl)-Thiazolidine-4-carboxylic acid | Thiazolidine |
|---|---|---|---|---|---|---|---|
| UV | − | + | − | − | + | − | − |
| Electrolysis | + | − | + | + | − | + | + |

As seen from table 1 above, the use of electrolysis alone will not suffice since this will bias the reaction to the formation of Cysteine and Cysteine hydrochloride from any Cystine and its derivatives that are formed by oxidation and over time. This will result in an abundance of Cysteine derivatives such as S-(2-Phenoxyethyl)Cysteine which then over time form Thiazolidine derivatives. UV radiation is necessary to decompose the Thiazolidines to free the Cysteine as reactive Cysteine for favorable formation of S-(2-Phenoxyethyl)Cysteine, which remains stable in the absence of UV and electrolysis after it is formed and the reaction is stopped in time. The end products of using percentage ingredients listed in Table 2 for a variety of times and exposure-levels are shown in Table 3.

First Preferred Embodiment

Figure 2:
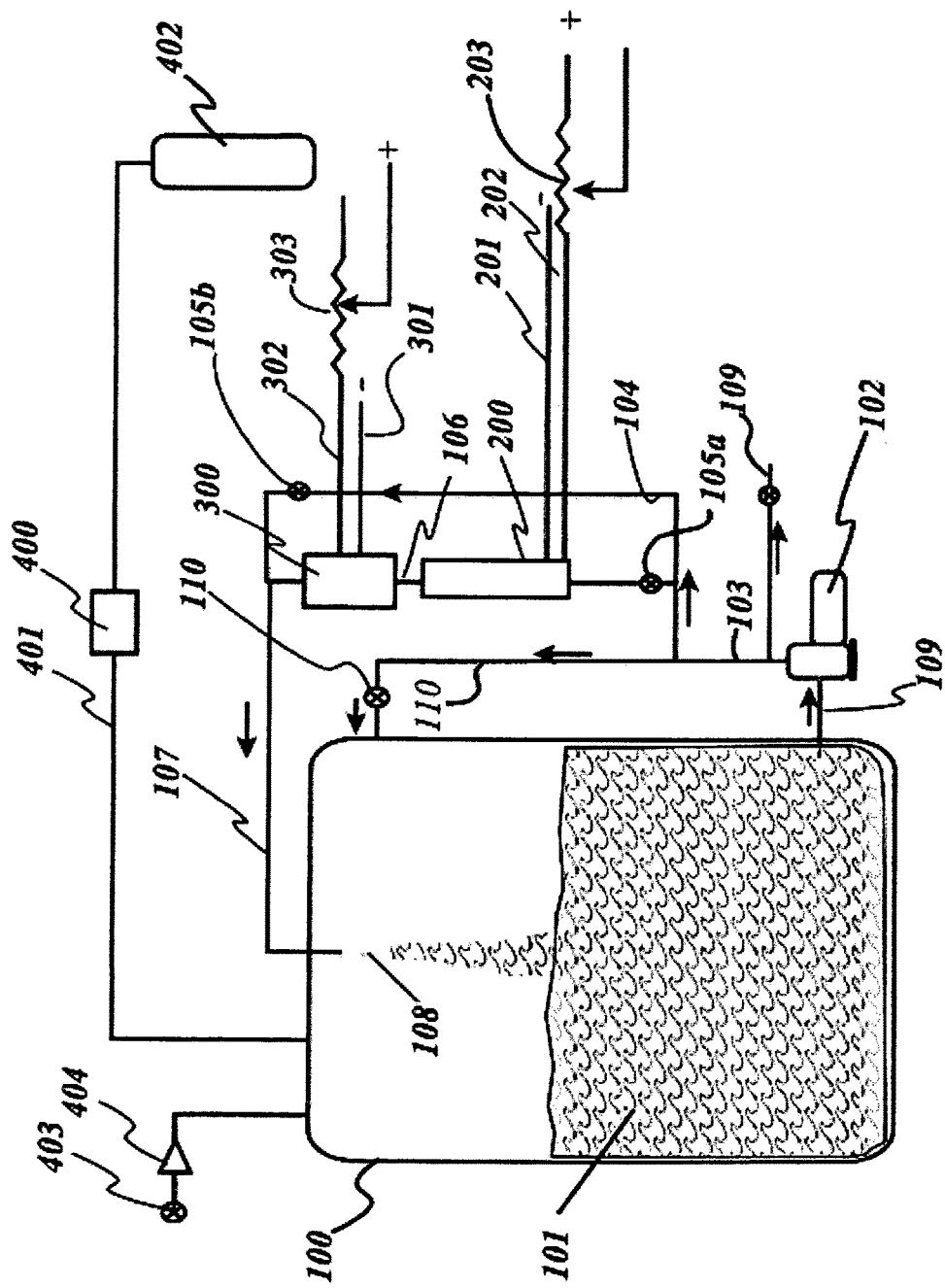
FIG. 2 is a drawing of the apparatus setup for manufacturing a variety of cosmetic solutions using UV light and electrolysis in a serial configuration.
Figure 3:
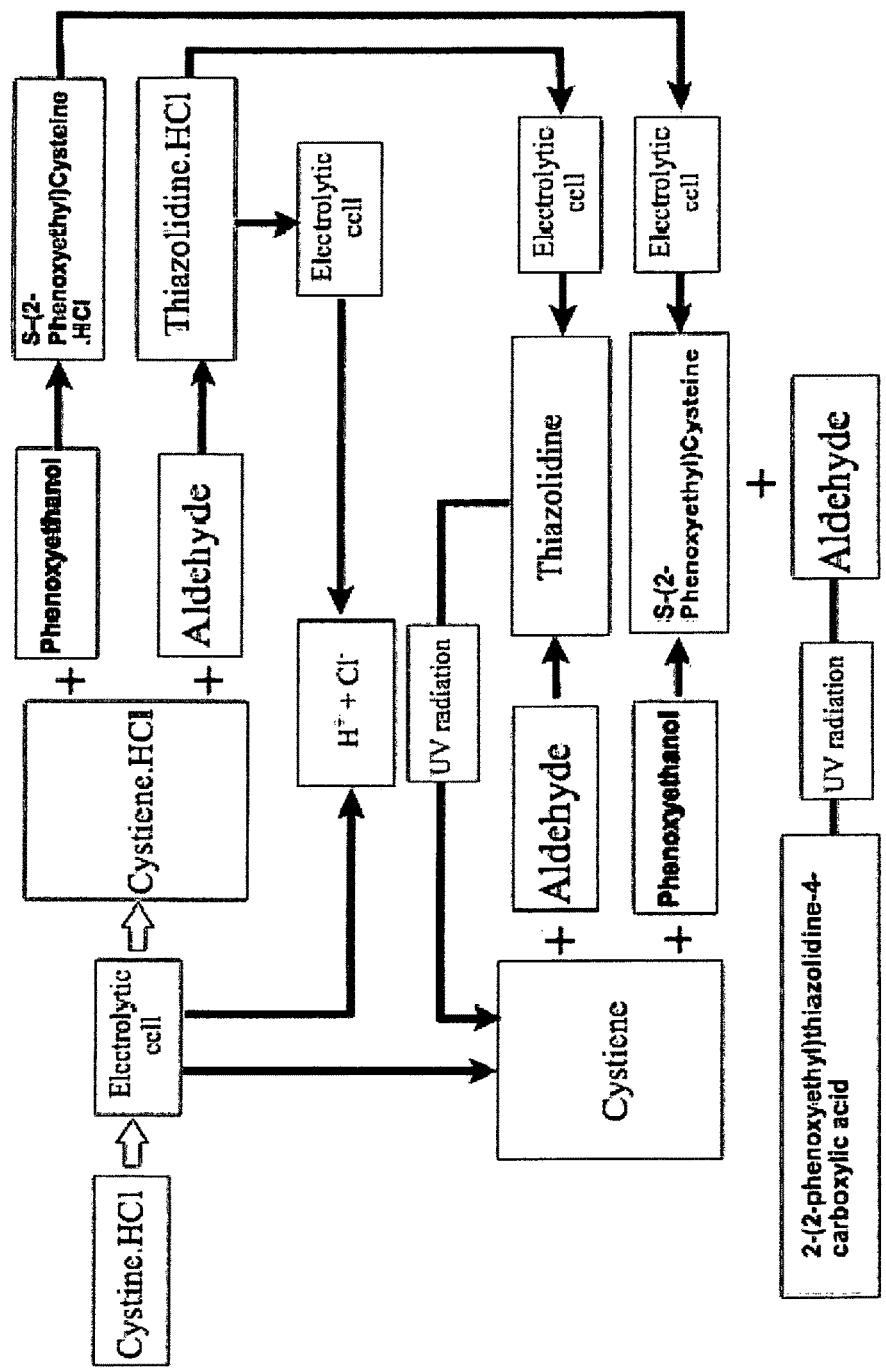
FIG. 3 is a flow chart showing the various reactions and effects of the UV radiator and the Electrolytic cell on reactants.

Referring to the various FIGURES, the preferred apparatus for practicing the present method is disclosed. FIG. 1 is a drawing showing one configuration of the manufacturing equipment needed to make solutions according to the present invention with the UV Radiator 200 and the Electrolytic cell 300 in series. This configuration allows the Electrolytic cell 300 to dissociate Cystine in close proximity to the UV radiator 200 to maximize the production of derivatives of Cysteine before the solution goes back into Tank 100. FIG. 2 shows the parallel configuration of the Electrolytic cell 300 and the UV Radiator 200. This makes the decomposition of Cystine independent of the end products formed since the any electrolytically decomposed Cystine and any UV decomposed thiazolidines will enter the tank and allow a free competition of reactants to react with Cysteine.

In FIG. 1, Tank 100 is used to store and process the cosmetic solution 101. Tank 100 is preferable a plastic tank. Valve 109 is used as a supply line for fluid components of solution 101 to Tank 100 as well as for emptying solution 101 from Tank 100. Valve 109 remains closed during the process. Cosmetic solution 101 comprises mixtures of ingredients in percentage ranges that can be used as shown in Table 2. A pump 102 connects to Tank 100 via suction pipe 109 to pump solution 101 and circulate it through pipes 103, pipe 104, pipe 106, and pipe 107. Pipe 103 supplies Pipe 104 through flow regulator 105. Pipe 103 also supplies solution 101 to pipe 106 through flow regulator 105. Pipe 104 supplies the flow of solution 101 to the UV Radiator 200. UV Radiator 200 is preferably one or more of a 150 Watt UV Radiators supplied by SMART HO UV Sterilizers made by Emperor Aquatics Inc., located at 2229 Saratoga Station Road, Pottstown, Pa. 19464. A series configuration of UV Radiators 200 may be incorporated if more UV power is needed. Solution 101 flows through UV Radiator 200 and exits to join flow from pipe 106. The combined flow enters Electrolytic cell 300. Electrolytic cell 300 is a de-chlorination electrolytic cell made by AquaCal AutoPilot, Inc., 2737 24th Street North, St. Petersburg, Fla. 33713. To have a desired effect, the Electrolytic cell 300 requires a minimum of 0.1 Joules/in$^3$ in energy density to act on Solution 100 at the minimum concentration of 0.3% Cysteine or its derivatives. Similarly, Electrolytic cell 300 requires a maximum of 500 Joules/in$^3$ of energy density at the maximum percentage concentration of 6% Cysteine or its derivatives in cosmetic. This reflects the amount of electrons needed to completely dissociate the amount of L-Cysteine hydrochloride, or the Cystine dimer. If a higher percentage of Cysteine is present, then more energy will be needed. In general, Electrolytic cell 300 needs about 87.7 Joules/in3 of energy delivery per percent of Cysteine content. To get a minimal effect of the UV light from UV Radiator 200 in one hour, an exposure of a minimum of 100 Joules/in$^3$ at the minimum percentage rage of 0.3% of L-Cysteine hydrochloride to 3000 Joules/in$^3$ of cosmetic solution 101 at the maximum percentage range of 6% Cysteine or its derivatives (L-Cysteine hydrochloride) in solution is required. This requires about 508 Joules/in$^3$ per percent of Cysteine present in solution 101. It is possible to use up to 10% of Cysteine or its derivatives with the invention as long as all the other reactants are scaled up proportionally.

Electrolytic cell 300 could also be configured to be multiple cells configured in series to increase the electrolysis capacity of Electrolytic cell 300. The combined flow from UV Radiator 200 and Electrolytic cell 300 is transported through pipe 107 to renter Tank 100 as a flow stream 108. Effectively greater than a 100 Joules/in$^3$ of total energy must be expended from UV Radiator 200 and Electrolytic cell 300 on solution 101 to get a minimal controlled effect on solution 101.

As shown in the diagram, the flow rate to the Electrolytic cell 300 may be increased or decreased by opening valve 105 to allow more of solution 101 to enter in the Electrolytic cell 300 than has passed through UV Radiator 200. Power cable 201 and power cable 202 both supply bipolar AC electricity to UV Radiator 200 through Rheostat controller 203. Power cable 301 and power Cable 302 supply electricity both supply bipolar AC electricity to Electrolytic cell 300 through Rheostat controller 303. Thus the power to each of the said components can be turned ON or OFF as needed. Flow regulator 110 regulates the return free flow into Tank 100 and thus can be used to regulate the total flow of solution 101 through both UV Radiator 200 and Electrolytic cell 300. Electrolytic cell 300 must generate a minimum of 0.1 Joules/in$^3$ of energy density of cosmetic solution at the minimum percentage range of 0.3% Cysteine or its derivative, L-Cysteine hydrochloride in solution 101 to have a desired effect, since the amount of electrons needed to completely dissociate the amount of L-Cysteine hydrochloride in this amount of solution 101 requires this amount of electrical energy to be consumed.

If the Hydrochloride of cysteine is used, then Chlorine gas and Hydrogen may be electrolytically generated by Electrolytic cell 300 at voltage levels greater than 5V. The removal of some Chlorine gas by the anode of the Electrolytic cell 300 at voltages greater than 5V can be effectuated by flowing excess gases from the Tank 100 through a condensation pipe 401 into a smaller separate chlorinating tank 402. Preferably a dosing pump 400 with a Solenoid-driven diaphragm made by Lutz-Jesco GmbH located in Wedemark, Germany, is used to remove excess Chlorine from the process Tank 100 and transfer it to the Chlorinator tank 402 containing water. Dosing pumps are used in many branches of industry that work with liquid chemicals including toxic and aggressive media. The Chlorine generated from the Electrolytic cell 300 is sucked from Tank 100 through process pipe 401 by dosing pump 400. Air is displaced into tank 400 through check valve 404. The vacuum created in process Tank 100 to replace the gases taken out by dosing pump 400, and no Chlorine (if the protected Cysteine is used), Sulfur, or Hydrogen gases are allowed escape into the atmosphere. The Chlorine gas that is generated if L-Cysteine hydrochloride is decomposition is passed through a series of water filled chlorinating tank 402 plastic containers to absorb the Chlorine and make HCl solution in chlorinator tank 402. The Hydrochloride (HCl) solution, can be used for cleaning purposes. Throughout the process run time of the Electrolytic cell 300, some Chlorine gas is continuously removed from the solution 101. To ensure that no pressure builds up in Tank 100 due to Chlorine and other gases that may be released, a pressure sensor is used to switch on dosing pump 400 when the pressure exceeds atmospheric pressure. Chlorinator pump 400 can be powered by electrical energy. In certain cases when the pressure of the Chlorine gas in Tank 100 is small, the gas could just be allowed to flow into Chlorinator tank 402 by its own pressure to be absorbed by water.

As an example of manufacturing 1000 kg of the cosmetic solution 101 percentages of ingredients shown in Table 2 are placed in the tank 101 as flows. The about 5 kg of Keratin powder is added to about 800 Kg of water in Tank 100; 7.88 kg of L-Cysteine monohydrochloride powder (the molar equivalent of 6.051 kg of Cysteine, Or 38.1 gram-moles) is added into the water and the resulting mixture is circulated by pump 102 while flow regulator 105 and flow regulator 105b are turned OFF so that nothing flows through either UV Radiator 200 or Electrolytic cell 300. Thirty-eight (38) mole grams of L-Cysteine hydrochloride corresponds to about $367.7 \times 10^{22}$ electrons or 21.2 KJ of energy in one hour of exposure to Electrolytic cell 300.

Pump 102 can be powered by a electricity as provided for by the manufacturer. A simple pool pump that can deliver up to 50 gallons per minute will suffice. The partially made solution 101 is circulated through Tank 100 until all the powders have dissolved. Hydrolyzed Keratin in liquid form can also be used, in which case about 50 kg of the liquefied form is added. Flow regulator 105a and flow regulator 105b are then opened to allow flow through UV Radiator 200 and Electrolytic cell 300. Both UV Radiator 200 and Electrolytic cell 300 are powered by 120 VAC power and have their own internal control electronics for self cleaning and current regulation as supplied by the manufacturers. By adjusting flow regulator 110, a continuous flow speed of between 100 in/s to 130-160 in/sec through the process pipe 104 ensures that an exposure radiation level of between 100 Joules/in$^3$ to 3000 Joules/in$^3$ can be achieved either using a single unit of UV Radiator 200 or a serial or parallel array of UV Radiator 200. UV Radiator 200 is usually nominally about 30 in in length. The intensity of UV radiation can vary depending on the density and opacity of the fluid comprising solution 101. However these factors can be nulled out by circulating the solution 101 to repeatedly expose every molecule of solution 101 to the radiation fields of UV Radiator 200. Varying the flow rate of flow regulator 105a will vary the delivery of energy in Watts/in and this in turn regulates total energy in Joules/in$^3$ delivered to effectively control the rate of decomposition of Thiazolidines compounds formed by reactions between Cysteine formed in situ by electrolysis and Glyoxylic acid or formaldehyde. Rheostat controller 303 can regulate the power to Electrolytic cell 300. This controls the rate of decomposition of Thiazolidines in solution 101. Thus, the yield of protected Thiazolidines in solution 101 can be balanced with the yield of unprotected species. The volume of the solution being processed directly determines the amount of time of exposure depending on the intensity of the UV Radiator 200 and the energy delivery rate of the Electrolytic cell 300. The rate of formation of S-(2-Phenoxyethyl)Cysteine is mostly dependent on the rate at which the rate of Cystine dimer formation from Cysteine can compete with Phenoxyethanol in solution 101. Thus, the rate of formation of both the dimer and S-(2-Phenoxyethyl) Cysteine can be regulated by physical means. The partially formed solution 101 mix is then circulated through with both an active UV Radiator and an active electrolytic cell. The mixture is circulated for at least five hours through both the Electrolytic cell 300 and UV Radiator 200 to allow hydrogen and Chlorine to be removed from the L-Cysteine monohydrochloride by electrolysis at a controlled rate. This process will give nearly 50-60% yield of Thiazolidines after 10 hours of operation and about 70%-80% S-(2-Phenoxyethyl) Cysteine yield. The remaining Glyoxylic acid will react with Cysteine and other sulfur amino compounds in keratin amino acids to yield other Thiazolidines compounds. Since the hydrochloride of Cysteine can also reform in solution 101, the extent of further electrolysis and the amount of UV radiation both determines the amount of unprotected yield of available Cysteine to form chlorides of Thiazolidines. If the solution 101 is left to continue running through the Electrolytic cell 300 for at least 15 hours the dimer Cystinehydrochloride will be mostly eliminated and all the Cysteine will be used up in reactions. Simply deciding the intensity and when to turn the Electrolytic cell 300 OFF can regulate the dimer concentration. Thus the amount of Thiazolidines formation can also be accurately regulated.

In general to make an example batch of 1000 kg of solution 101, about 40 kg of Cyclomethicone and Dimethicone, 20 kg of Guar Gum, 2 kg Behentrimonium chloride, 2 kg of Cetrimonium chloride, 10 kg of Butylene Glycol, 10 kg of Glycolic acid, 10 kg of Propylene Glycol is further added into the circulating heated water and the resulting mixture is circulated for an additional period of time but not less than one hour, until all the waxes have melted completely and a homogenous mixture is obtained. The additional amount of water added is calculated to bring up the total weight of solution A to 1000 kg after all the ingredients are accounted for. Thus it is preferable to start with about 800 kg of water if a batch of 1000 kg of solution A is to be made. The gums and waxes can adjusted in the solution 101 to give the desired viscosity of between 1000 cps to 5000 cps at room temperature (78° F.). The solution 101 is then left to cool to room temperature with the UV radiator 200 and Electrolytic cell 300 turned off.

FIG. 2 shows a parallel configuration of the UV radiator 200 and Electrolytic cell 300. In this configuration, using a series of parallel or serially configured UV radiators, one can achieve the desired intensity of energy delivery density to maximize the amount of solution 101 that can be processed. Electrolytic cell 300 and UV Radiator 200 can be adjusted independently to achieve various effects. Apart from being able to change the flow rate to adjust the intensity of UV Radiator 200 and Electrolytic cell 300, the flow rate can now be adjusted to allow the exposure times to be varied as desired.

The parallel configuration shown in FIG. 2 can be used to maximize the yield of S-(2-Phenoxyethyl)Cysteine yield since the UV Radiator 200 decomposes thiazolidines and the Electrolytic cell 300 decomposes Cystine and maximizes the yield of Cysteine in the returning solution 101 to assists the reactions of Phenoxyethanol with Cysteine.

In the serial configuration shown in FIG. 1, the position of the UV radiator 200 and Electrolytic cell 300 can impact the formation of compounds. For example if the Solution 101 encounters the Electrolytic cell 300 before UV Radiator 200, then Cystine will be electrolytically decomposed to Cysteine and made available for reactions that are assisted by UV Radiator 200. The thiazolidine rings will be deterred by the UV radiator 200 and thus, depending on the flow rate, it is also possible to form a high yield of S-(2-Phenoxyethyl) Cysteine with this configuration.

If the UV Radiator is encountered by the flow before the Electrolytic cell 300, then hydrochlorides of cysteine derivatives will be formed first and then decomposed to yield a chlorine and hydrogen by electrolysis. This will include Cystine hydrochloride since the Electrolytic cell 300 will preferably decompose the hydrochlorides before decomposing Cysteine.

Taking into account the percentage of L-Cysteine hydrochloride in solution 101, effectively more than 100 Joules/in3 of energy must be expended from heating, UV Radiator 200, and Electrolytic cell 300 on solution 101 to get a full range of minimal controlled effects on solution 101. The UV radiation energy absorbed by the solution 101 cannot exceed 3000 Joules/in$^3$ of solution when combined with heating of the solution, otherwise the ingredients would start to disintegrate and water will start to boil off from the reaction tank. However this does not limit the invention, since in some cases, depending on the initial temperature of the water, a higher intensity can be used to achieve the heating. UV radiator cannot exceed an energy density of 7000 Joules/in$^3$ since this will boil the solution 101. A higher UV power source simply makes the process go faster. A higher electrolysis rate would simply make the process go faster, however at about 500 Joules/in$^3$ there is a danger of too a high rate of production of explosive gases in the process tank. Effectively, although the relationship of energy versus Cysteine content is not linear, about between 100 Joules/in3 to 1000 Joules/in$^3$ of UV radiation and between 0.1 Joules/in$^3$ to 16 Joules/in$^3$ of electrolytic energy per each percent of L-Cysteine hydrochloride of solution 101 is needed for a variety of desired minimal effects; Solution 101 requires keratin, Cysteine, Phenoxyethanol and an aldehyde such as one of Formaldehyde and Glyoxylic acid, or a combination of both thereof, to generate all possible effects.

Further, the order of the flow exposure between UV Radiator 200 and Electrolytic cell 300 shown in FIG. 1 can be rearranged to have the desired chemistry effects on the solution 101 and its ingredients.

In so far as it is possible to have direct UV light exposure to the contents of the Tank 100, the invention teaches many more modes of achieving the same desired goals without limiting the scope.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

TABLE 2

| Ingredient | % Range by Weight | % Range by Weight | % Range by Weight | % Range by Weight | % Range by Weight |
| --- | --- | --- | --- | --- | --- |
| Water and scented oils (ex. Arnica Montana Flower) | Up to 100% | Up to 100% | Up to 100% | Up to 100% | Up to 100% |
| Hydrolyzed Keratin | 0.2%-0.5% | 0.2%-0.5% | 0.2%-0.5% | 0.2%-0.5% | 0.2%-0.5% |
| Cysteine and or pure L-Cysteine monohydrochloride | 0.3%-6.0% | 0.3%-6.0% | 0.3%-6.0% | 0.3%-6.0% | 0.3%-6.0% |
| Formaldehyde and or Glyoxylic acid | 1%-10.0% | 1%-10.0% | 1%-10.0% | 1%-10.0% | 1%-10.0% |
| Phenoxyethanol | 1.0%-2.0% | 1.0%-2.0% | 1.0%-2.0% | 1.0%-2.0% | 1.0%-2.0% |
| Equal blend of Cyclomethicone and Dimethicone | 1.0%-2.0% | 1.0%-2.0% | 1.0%-2.0% | 1.0%-2.0% | 1.0%-2.0% |
| Guar Gum | 1.0%-3.0% | 1.0%-3.0% | 1.0%-3.0% | 1.0%-3.0% | 1.0%-3.0% |
| Behentrimonium Chloride, | 0.0%-0.5% | 0.0%-0.5% | 0.0%-0.5% | 0.0%-0.5% | 0.0%-0.5% |
| Phenyltrimethicone (Dow, 2-2078 fluid) | 0.2%-0.5% | 0.2%-0.5% | 0.2%-0.5% | 0.2%-0.5% | 0.2%-0.5% |
| Cetrimonium Chloride | 0.0%-0.5% | 0.0%-0.5% | 0.0%-0.5% | 0.0%-0.5% | 0.0%-0.5% |
| Glycolic acid | 0.0%-2.0% | 0.0%-2.0% | 0.0%-2.0% | 0.0%-2.0% | 0.0%-2.0% |
| Propylene Glycol | 0.0%-1.0% | 0.0%-1.0% | 0.0%-1.0% | 0.0%-1.0% | 0.0%-1.0% |
| Cetyl Stearyl alcohol | 0.5%-8.0% | 0.5%-8.0% | 0.5%-8.0% | 0.5%-8.0% | 0.5%-8.0% |
| Xanthan Gum | 0.0%-0.3% | 0.0%-0.3% | 0%-0.3% | 0.0%-0.3% | 0.0%-0.3% |
| Caprylyl Methicone | 0.0%-0.3% | 0.0%-0.3% | 0.0%-0.3% | 0.0%-0.3% | 0.0%-0.3% |

TABLE 3

Resulting products based on % ingredients and exposure levels to UV radiation and Electrolysis over time.

| UV exposure time | 10 hrs | 10 hrs | 0 hrs | 10 hrs | 15 hrs |
| --- | --- | --- | --- | --- | --- |
| UV exposure energy density level | 200 Joules/in$^3$ | 300 Joules/in$^3$ | 100 Joules/in$^3$ | 2000 Joules/in$^3$ | 3000 Joules/in$^3$ |
| | Heat to 150° F. | Heat to 150° F. | Heat to 150° F. | no heating | no heating |

TABLE 3-continued

Resulting products based on % ingredients and exposure levels to UV radiation and Electrolysis over time.

| | | | | | |
|---|---|---|---|---|---|
| Electrolysis exposure 0.1 Joules/in$^3$ | 10 hrs | 10 hrs | 10 hrs | 0 hrs | 15 hrs |
| Electrolysis exposure 100 Joules/in$^3$ | 1 hr | 1 hr | 1 hr | 0 hr | 1.5 hrs |
| Thiazolidine yield per mole of L-Cysteine monohydrochloride | 40%-50% | 65%-75% | 80%-90% | 5%-10% | 65%-75% |
| S-(2-Phenoxyethyl)Cysteine yield per mole of Phenoxyethanol | 60%-70% | 50%-60% | 30%-40% | 80%-90% | 80%-90% |
| 2-(2-Phenoxyethyl)Thiazolidine-4-carboxylic acid yield per mole of Phenoxyethanol | 10%-20% | 10%-20% | 15%-25% | 10%-20% | 1.0%-5.0% |
| Protected Thiazolidine-hydrochlorides yield per 2 moles of L-Cysteine monohydrochloride | 30%-40% | 15%-25% | 20%-30% | 1%-5% | 1%-5% |
| Lanthionine yield per 2 moles of L-Cysteine monohydrochloride Cysteine | 0.0%-1.0% | 2.0%-5.0% | 0% | 10%-15% | 15%-20% |
| Cystine per 2 moles of L-Cysteine monohydrochloride | 5.0%-9.0% | 4.0%-5.0% | 2.0%-5.0% | 25%-30% | 1.0%-2.0% |
| Other Cysteine reacted components | <1% | <5% | <5% | <3% | <1% |

I claim as my invention:

1. A method of transforming a first cosmetic solution into a second cosmetic solution for producing a cosmetic product, the method comprising:
   providing a first cosmetic solution comprising about 0.3 to about 6.0 percent by weight of any relative proportion of cysteine and L-cysteine hydrochloride; about 0.2 to about 0.5 percent by weight of a hydrolyzed keratin; about 1.0 to about 2.0 percent by weight of phenoxyethanol; about 1.0 to about 10.0 percent by weight of any relative proportion of formaldehyde and glyoxylic acid; and water;
   circulating the first cosmetic solution such that cysteine reacts with at least one of formaldehyde and glyoxylic acid to form a thiazolidine, and such that a cystine dimer is formed by oxidation, and such that S-(2-phenoxyethyl) cysteine is formed from cysteine and phenoxyethanol;
   circulating the first cosmetic solution through an active electrolytic cell which delivers to the first cosmetic solution an energy density in the range of 0.1 to 100 Joules/in$^3$; and
   circulating the first cosmetic solution through ultraviolet light which delivers to the first cosmetic solution an energy density in the range of 100 to 3000 Joules/in$^3$, thereby transforming the first cosmetic solution to a second cosmetic solution.

2. The method of claim 1, wherein the first cosmetic solution flows in fluid circuit.

3. The method of claim 2, wherein the flow rate of the fluid circuit is controlled by a circulating pump and at least a flow rate control valve.

4. The method of claim 1, wherein the second cosmetic solution further comprises at least one of: cyclomethicone, dimethicone, an alcohol wax, and a natural gum.

5. The method of claim 4, wherein the natural gum comprises guar gum.

6. The method of claim 1, further comprising: providing a means for selectively modifying the intensity of electric current to the ultraviolet light source and to the electrolytic cell and modifying the flow rate of the fluid circuit by operating the flow rate control valve, to alter the effect of ultraviolet light to selectively produce at least one of a plurality of grades of a second cosmetic product.

7. The method of claim 1, wherein the cysteine dimer is then electrolytically dissociated back to a cysteine monomer using an electrolytic cell.

8. The method of claim 1, further comprising adding about 1 to about 4 percent by weight of an equal blend of cyclomethicone and dimethicone to the second cosmetic solution to produce a cosmetic product for imparting shine and lubrication to human hair.

9. The method of claim 1, further comprising adding about 1 to about 4 percent by weight of guar gum to the second cosmetic solution.

10. The method of claim 9, wherein the guar gum is non-cationic.

11. The method of claim 9, wherein the guar gum is made from food grade gums.

12. The method of claim 1, further comprising adding about 0.5 to 8 about percent by weight of cetyl stearyl alcohol to the second cosmetic solution.

13. The method of claim 1, wherein the quantity of first cosmetic solution additionally comprises a second component comprising about 0.25 to about 0.5 percent by weight of behentrimonium chloride.

14. The method of claim 1, further comprising adding about 0.2 to about 0.5 percent by weight of cetrimonium chloride to the second cosmetic solution.

15. The method of claim 1, further comprising adding about 1 to about 2 percent by weight of butylene glycol to the second cosmetic solution.

16. The method of claim 1, further comprising adding about 0.5 to about 1 percent by weight of propylene glycol to the second solution.

17. The method of claim 1, further comprising adding about 0 to about 2 percent by weight of glycolic acid to the second solution.

18. The method of claim 1, further comprising adding about 0 to about 0.3 percent by weight of caprylyl methicone to the second solution.

19. The method of claim 1, further comprising adding about 0 to about 0.3 percent by weight of xanthan gum.

20. The method of claim 1, further comprising adding about 0.2 to about 0.5 percent by weight of behentrimonium chloride to the second cosmetic solution.

21. The method of claim 1, further comprising adding about 0.2 to about 0.5 percent by weight of phenyltrimethicone to the second cosmetic solution.

22. The method of claim 1, further comprising adding about 0.2 to about 0.5 percent by weight of cetrimonium chloride to the second cosmetic solution.

23. The method of claim 1, further comprising adding about 0 to about 2.0 percent by weight of butylene glycol to second cosmetic solution.

24. The method of claim 1, wherein the first cosmetic solution further comprises about 0.5 percent by weight of propylene glycol.

25. The method of claim 1, further comprising providing a plastic tank and preparing the first cosmetic solution in the plastic tank to eliminate the loss of electrostatic potentials by conductivity.

26. The method of claim 1, further comprising flowing excess gases from the solution through a condensation pipe into a separate chlorinator tank.

27. A method of preparing and transforming an initial cosmetic solution to create any of a variety of cosmetic products, comprising the steps of:
preparing an initial cosmetic solution comprising substantially at least 80% water; heating the water to substantially 150 degrees F.; adding to the heated water a quantity of 0.2 to 0.5 percent by weight of hydrolyzed keratin powder; 0.3 to 6 percent by weight of at least one of Cysteine and L-Cysteine; 1%-10 percent by weight of at least one of formaldehyde and Glyoxylic acid; 1 to 2 percent by weight of Phenoxyethanol; circulating the initial cosmetic solution such that it is thoroughly mixed; wherein Thiazolidines are formed by reactions of Cysteine and at least one of formaldehyde and Glyoxylic acid, and whereas Cystine dimer is formed by oxidation of Cysteine in the initial cosmetic solution and whereas S-(2-Phenoxyethyl) Cysteine is formed by reactions of Cysteine and Phenoxyethanol; circulating the initial cosmetic solution through an active electrolytic cell which delivers to the initial cosmetic solution an energy density in the range of 0.1 to 100 Joules/in$^3$ and through ultraviolet light which delivers to the initial cosmetic solution an energy density in the range of 100 to 3000 Joules/in$^3$.

28. The method of claim 27, wherein the hydrolyzed keratin is at least one of hydrolyzed keratin powder and hydrolyzed keratin liquid.

29. The method of claim 27, wherein the energy density delivered by the electrolytic cell to the initial cosmetic solution is adjustable.

30. The method of claim 27, wherein the energy density delivered by the ultraviolet light to the initial cosmetic solution is adjustable.

31. The method of claim 27, whereas the amount of electrolytic energy delivered to the initial cosmetic solution is 50 to 100 Joules/in$^3$ and the amount of ultraviolet light energy delivered to the initial cosmetic solution is 2000 to 3000 Joules/in$^3$, such that Cystine dimer chemically formed in the initial cosmetic solution is decomposed to Cysteine by electrolysis and such that Thiazolidines chemically formed with Cysteine are decomposed back to Cysteine by ultraviolet light and such that the Cysteine is made available and reacts with Phenoxyethanol to maximize the yield of S-(2-Phenoxyethyl) Cysteine in the initial cosmetic solution.

32. The method of claim 27, wherein by adjusting the energy density of the electrolytic cell the amount of yield of Cysteine from Cystine dimer is regulated.

33. The method of claim 27, wherein by adjusting the energy density of the ultraviolet light, the amount of yield of Cysteine from Thiazolidines is regulated.

34. The method of claim 27, wherein by adjusting the energy density of the ultraviolet light the amount of yield of S-(2-Phenoxyethyl) Cysteine is regulated.

35. The method of claim 27, whereas the amount of electrolytic energy delivered to the initial cosmetic solution is 50 to 100 Joules/in$^3$ and the amount of ultraviolet light energy delivered to the initial cosmetic solution is less than 300 Joules/in$^3$, such that Cystine dimer chemically formed in the initial cosmetic solution is decomposed to Cysteine by electrolysis and such that the Cysteine preferentially reacts with one of at least formaldehyde and Glyoxylic acid to form Thiazolidines, and such that the Thiazolidines are not decomposed by ultraviolet light and such that the yield of Thiazolidines in the initial cosmetic solution is maximized.

36. The method of claim 27, comprising the additional step of circulating the solution for at least five hours through both ultraviolet light exposure and an electrolytic cell to permit hydrogen and Chlorine to be removed from the L-Cysteine monohydrochloride by electrolysis and to decompose the L-Cystine monohydrochloride back to the monomer as available Cysteine for reactions.

37. The method of claim 27, wherein the solution is circulated through the electrolytic cell for at least ten hours such that Thiazolidines carboxylic acid derivatives of L-Cysteine monohydrochloride are formed.

* * * * *